(12) United States Patent
Harvey et al.

(10) Patent No.: US 12,223,980 B2
(45) Date of Patent: Feb. 11, 2025

(54) METHODS AND APPARATUS FOR HEADSET DIAGNOSTICS

(71) Applicant: Cirrus Logic International Semiconductor Ltd., Edinburgh (GB)

(72) Inventors: Thomas I. Harvey, Edinburgh (GB); John P. Lesso, Edinburgh (GB)

(73) Assignee: Cirrus Logic Inc., Austin, TX (US)

( * ) Notice: Subject to any disclaimer, the term of this patent is extended or adjusted under 35 U.S.C. 154(b) by 981 days.

(21) Appl. No.: 17/065,219

(22) Filed: Oct. 7, 2020

(65) Prior Publication Data

US 2021/0136503 A1 May 6, 2021

Related U.S. Application Data

(60) Provisional application No. 62/945,986, filed on Dec. 10, 2019, provisional application No. 62/930,214, filed on Nov. 4, 2019.

(51) Int. Cl.

| | | |
|---|---|---|
| H04R 25/00 | (2006.01) | |
| A61B 5/117 | (2016.01) | |
| G02B 27/01 | (2006.01) | |
| G06F 3/01 | (2006.01) | |
| G10L 25/51 | (2013.01) | |

(Continued)

(52) U.S. Cl.
CPC ............. *G10L 25/51* (2013.01); *A61B 5/117* (2013.01); *G02B 27/017* (2013.01); *G06F 3/012* (2013.01); *H04R 1/023* (2013.01); *H04R 1/1041* (2013.01); *H04R 3/04* (2013.01); *H04R 25/654* (2013.01); *H04R 2460/01* (2013.01)

(58) Field of Classification Search
CPC .... H04R 1/023; H04R 1/1041; H04R 25/654; H04R 29/001; H04R 29/004; H04R 2460/01; H04R 1/1016; H04R 1/1025; H04R 3/04; H04R 25/30; H04R 2225/31; H04R 2460/13
See application file for complete search history.

(56) References Cited

U.S. PATENT DOCUMENTS 5,253,300 A * 10/1993 Knapp ................. H04R 25/602
  381/328
7,003,128 B2 * 2/2006 Boonen .................. H04R 25/30
  381/322

(Continued)

FOREIGN PATENT DOCUMENTS

| CN | 109413557 A | 3/2019 |
| EP | 1333701 A2 | 8/2003 |

(Continued)

OTHER PUBLICATIONS

International Search Report and Written Opinion of the International Searching Authority, International Application No. PCT/GB2020/052290, mailed Nov. 19, 2020.

(Continued)

*Primary Examiner* — Huyen D Le
(74) *Attorney, Agent, or Firm* — Jackson Walker L.L.P.

(57) ABSTRACT

A method for diagnosing a condition of a first headset enclosed in a headset enclosure. The method comprises playing a first audio stimulus through a first speaker of the headset; detecting a first response signal derived by a first transducer; and determining a condition of the first speaker and/or first transducer based on the first response signal.

22 Claims, 13 Drawing Sheets

(51) Int. Cl.
*H04R 1/02* (2006.01)
*H04R 1/10* (2006.01)
*H04R 3/04* (2006.01)

(56) References Cited

U.S. PATENT DOCUMENTS

| | | | | |
|---|---|---|---|---|
| 7,609,026 | B2* | 10/2009 | Tsunoda | H02J 7/0044 |
| | | | | 381/370 |
| 8,538,050 | B2* | 9/2013 | Fink | H04R 25/30 |
| | | | | 381/314 |
| 9,838,812 | B1 | 12/2017 | Shetye et al. | |
| 10,097,914 | B2 | 10/2018 | Petrank | |
| 10,424,955 | B2* | 9/2019 | Higgins | H02J 7/0044 |
| 11,189,300 | B2* | 11/2021 | Harvey | H04R 1/1041 |
| 11,431,185 | B1* | 8/2022 | Feng | H02J 7/007 |
| 11,615,803 | B2* | 3/2023 | Harvey | H04R 1/023 |
| | | | | 381/56 |
| 2004/0196992 | A1* | 10/2004 | Ryan | H04R 5/033 |
| | | | | 381/317 |
| 2004/0202333 | A1 | 10/2004 | Csermak et al. | |
| 2019/0080682 | A1* | 3/2019 | Darlington | H04R 1/1083 |
| 2019/0294769 | A1* | 9/2019 | Lesso | G06F 21/32 |
| 2021/0248403 | A1* | 8/2021 | Harvey | G06V 40/10 |
| 2023/0058320 | A1* | 2/2023 | Harvey | G06F 3/167 |

FOREIGN PATENT DOCUMENTS

| | | |
|---|---|---|
| EP | 1865746 A2 | 12/2007 |
| EP | 4011095 A1 | 2/2021 |
| EP | 4049465 A1 | 4/2021 |
| WO | 2018129242 A1 | 7/2018 |

OTHER PUBLICATIONS

Examination Report under Section 18(3), UKIPO, Application No. GB2206793.8, mailed Jun. 29, 2023.

\* cited by examiner

METHODS AND APPARATUS FOR HEADSET DIAGNOSTICS

The present disclosure claims priority to U.S. Provisional Patent Application Ser. No. 62/945,986, filed Dec. 10, 2019, and U.S. Provisional Patent Application Ser. No. 62/930,214, filed Nov. 4, 2019, each of which is incorporated by reference herein in its entirety.

TECHNICAL FIELD

Embodiments of the disclosure relate to methods, apparatus and systems for personal audio device diagnostics, and in particular, for diagnosing a condition of a personal audio device, such as a headset, enclosed in an acoustic enclosure.

BACKGROUND

During manufacture of earphones, the earphones are generally placed in an acoustic test enclosure to determine a response characterisation of the earphones, which is then pre-programmed into the earphone and used for performance enhancement measures, such as acoustic noise cancellation (ANC), sidetone injection and the like. The acoustic test enclosure typically comprises a speaker and one or two microphones. When placed inside the acoustic test enclosure, an acoustic stimulus is output from the acoustic test enclosure speaker and recorded by one or two microphones of the earphone under test and an acoustic stimulus is applied to the earphone speaker and recorded at the microphone(s) of the acoustic test enclosure. The response characteristics of the earphones are then determined from the recorded signals and pre-programmed into the earphones.

However, deterioration of one or more components of the headsets can lead to a change in the response characteristics of the earphones, which impacts the effectiveness of ANC, sidetone injection etc., which rely on the response characteristics pre-programmed into the earphones.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

According to an aspect of the disclosure, there is provided a method for diagnosing a condition of a first headset enclosed in a headset enclosure, the method comprising: playing a first audio stimulus through a first speaker of the headset; detecting a first response signal derived by a first transducer; and determining a condition of the first speaker and/or first transducer based on the first response signal.

In some embodiments, determining the condition comprises comparing the first response signal to a template first response signal. For example, determining the condition further comprises extracting one or more features of the first response signal, and wherein comparing the first response signal to the template first response signal comprises comparing the one or more features extracted features with a corresponding template feature, the corresponding template features representing an optimal condition of the acoustic path or a previous condition of the acoustic path.

In some embodiments, the first transducer is the first speaker. The method may comprise determining that the first response signal corresponds substantially to a template response signal; and determining the condition of the first speaker as being not impaired. The method may comprise determining that the first response signal does not correspond substantially to a template first response signal; and determining the condition of the first speaker as being impaired. The method may comprise detecting a second response signal to the first audio stimulus derived by a second speaker; determining that the second response signal does not correspond substantially to the template second response signal; and determining a condition of the second speaker as being impaired. In some embodiments, the method may further comprising using the first speaker to compensate for the second speaker.

The method may comprise playing a second audio stimulus through a second speaker of the headset; detecting a third response signal to the second audio stimulus derived by the second speaker; determining that the third response signal corresponds substantially to the template third response signal; and using the second speaker to compensate for the first speaker.

The method may comprise detecting a fourth response signal to the first audio stimulus derived by a first microphone; and determining a condition of the first microphone based on the fourth response signal. Determining the condition of the first microphone may comprise determining that the fourth response signal corresponds substantially to a template fourth response signal; and determining the condition of the first microphone as being not impaired. Determining the condition of the first microphone may comprise determining that the fourth response signal does not correspond substantially to the template fourth response signal; and determining the condition of the first microphone as being impaired. The method may further comprise using the first speaker to compensate for the first microphone.

In some embodiments, determining the first response signal comprises receiving, at a processor of the enclosure, the first response signal from the first headset enclosed in the headset enclosure. Determining the second response signal may comprise receiving, at a processor of the enclosure, the second response signal from the first headset or from a second headset enclosed in the headset enclosure. Determining the second response signal may comprise receiving, at a processor of the enclosure, the second response signal from a second headset enclosed in the headset enclosure. Determining the fourth response signal may comprise receiving, at a processor of the enclosure, the fourth response signal from the first headset or a second headset enclosed in the headset enclosure.

In some embodiments, the first transducer is a first microphone. The method may comprise determining that the first response signal corresponds substantially to a template first response signal; and determining the condition of the first microphone as being not impaired and a condition of the first speaker as being not impaired. The method may comprise determining that the first response signal does not correspond substantially to a template first response signal; and determining the condition of the first microphone as being potentially impaired and the condition of the first speaker as being potentially impaired. The method may comprise detecting a second response signal derived by a second microphone; and determining the condition of the first speaker and/or the first microphone and/or the second microphone based on the second response signal. The method may comprise determining that the second response signal corresponds substantially to a template second response signal; and determining the condition of the first microphone as being impaired, the condition of the first speaker as being not impaired and a condition of the second microphone as being not impaired. In some embodiments, the method may comprise using the first speaker and/or the second microphone to compensate for the first microphone.

In some embodiments, the method comprises determining that the second response signal does not correspond substantially to a template second response signal; and determining the condition of the second microphone as being potentially impaired. In some embodiments, the method comprises determining that the second response signal does not correspond substantially to a template second response signal; and determining the condition of the first speaker as being impaired, the condition of the first microphone as being unimpaired and a condition of the second microphone as being unimpaired.

In some embodiments, the method comprises detecting a third response signal derived by a third microphone; and determining the condition of the first speaker and/or the first microphone and/or the second microphone and/or the third microphone based on the third response signal. The method may comprise determining that the third response signal does not correspond substantially to a template third response signal; and determining the condition of the first speaker as impaired.

In some embodiments, the method comprises detecting a fourth response signal derived by the first speaker; and determining a condition of the first speaker and/or the condition of the first microphone based on the fourth response signal. The method may comprise determining that the fourth response signal does not correspond substantially to a template fourth response signal; and determining the condition of the first speaker as impaired. The method may comprise determining that the fourth response signal does not correspond substantially to a template fourth response signal; and determining the condition of the first speaker as impaired and the condition of the first microphone as unimpaired.

In some embodiments, the method comprises playing a second audio stimulus through a second speaker of the headset, detecting a fifth response signal to the second audio stimulus derived by the second speaker; determining that the fifth response signal corresponds substantially to the template fifth response signal; and using the second speaker to compensate for the first speaker and/or the first microphone.

In some embodiments, determining the first response signal comprises receiving, at a processor of the enclosure, the first response signal from the first headset enclosed in the headset enclosure. Determining the second response signal may comprise receiving, at a processor of the enclosure, the second response signal from the first headset or from a second headset enclosed in the headset enclosure. Determining the third response signal may comprise receiving, at a processor of the enclosure, the third response signal from the first headset or a second headset enclosed in the headset enclosure. Determining the fourth response signal may comprise receiving, at a processor of the enclosure, the fourth response signal from the first headset enclosed in the headset enclosure. Determining the fifth response signal may comprise receiving, at a processor of the enclosure, the fifth response signal from a second headset enclosed in the headset enclosure.

In some embodiments, the first transducer is a second speaker. The method may comprise determining that the first response signal corresponds substantially to a template first response signal; and determining the condition of the first speaker as being not impaired and a condition of the second speaker as being not impaired. The method may comprise determining that the first response signal does not correspond substantially to a template first response signal; and determining the condition of the first speaker as being potentially impaired and a condition of the second speaker as being potentially impaired.

In some embodiments, the method may comprise detecting a second response signal derived by a first microphone; and determining the condition of the first speaker and/or the first microphone and/or the second speaker based on the second response signal. The method may comprise determining that the second response signal does not correspond substantially to a template second response signal; and determining the condition of the first speaker as impaired.

In some embodiments, determining the first response signal comprises receiving, at a processor of the enclosure, the first response signal from a second headset enclosed in the headset enclosure. Determining the second response signal may comprise receiving, at a processor of the enclosure, the second response signal from the first headset or from a second headset enclosed in the headset enclosure.

According to an aspect of the disclosure, there is provided an apparatus, comprising processing circuitry and a non-transitory machine-readable which, when executed by the processing circuitry, cause the apparatus to perform any one of the described methods. The apparatus may comprise a headset enclosure having a known acoustic environment. The headset enclosure may be a charging case for one or more headsets. The apparatus may comprise one or more of the first speaker, the second speaker, the first microphone, the second microphone and the third microphone.

According to an aspect of the disclosure, there is provided a non-transitory machine-readable medium storing instructions which, when executed by one or more processors, cause an electronic apparatus to perform any one of the described methods.

According to an aspect of the disclosure, there is provided a headset enclosure comprising: a body disposed within the enclosure; a first recess disposed in the body and arranged to receive a first earphone comprising a first speaker; a second recess disposed in the body and arranged to receive a second earphone comprising a second speaker; and wherein the body is configured such that the first speaker is orientated towards the second speaker when the first and second earphone are received by the respective first and second recesses.

The headset enclosure may comprise one or more transceivers for communicating with one or more headsets disposed within the enclosure; one or more processors; and memory storing instructions, which when executed by the one or more processors, causes the electronic circuitry to perform any one of the described methods.

According to an aspect of the disclosure, there is provided an electronic device, comprising the apparatus described above.

According to an aspect of the disclosure, there is provided an non-transitory machine-readable medium storing instructions which, when executed by one or more processors, cause an electronic apparatus to:

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the present disclosure will now be described by way of non-limiting example only with reference to the accompanying drawings, in which.

DESCRIPTION OF EMBODIMENTS

Embodiments of the disclosure relate to methods, apparatus and systems for personal audio device diagnostics, and in particular, for diagnosing a condition of a personal audio device, such as a headset, enclosed in an acoustic enclosure.

It has been recognised by the inventors that an acoustic enclosure, such as a charging case, is similar to an acoustic test enclosure in that it provides for an acoustic environment that is substantially free from noise and good for calibration purposes. Furthermore, with an acoustic enclosure arranged to receive a pair of earphones (as is typical of a charging case), a speaker and/or microphone(s) of another earphone are sufficiently nearby to provide for redundancy in diagnostic testing.

Diagnostics can be run at any time when the earphones are enclosed in the enclosure. For example, a diagnostic process may be performed periodically, and changes in the condition of components of the earphones can be monitored overtime. For example, the condition may be impaired (or faulty), not impaired (working correctly), and/or may indicate a degree of degradation.

Diagnostics data may be acquired by a personal audio device enclosed within an acoustic enclosure by the generation of an acoustic stimulus, and the detection of an acoustic response of one or more transducer(s) to the acoustic stimulus. One or more features may be extracted from the response signal(s), and used to diagnose one or more components of a personal audio device, such as a headset. The acoustic stimulus may be generated and the response measured using the personal audio device.

As used herein, the term "personal audio device" is any electronic device which is suitable for, or configurable to, provide audio playback substantially to only a single user. Some examples of suitable personal audio devices are shown in FIGS. 1a to 1e.

Figure 1A:
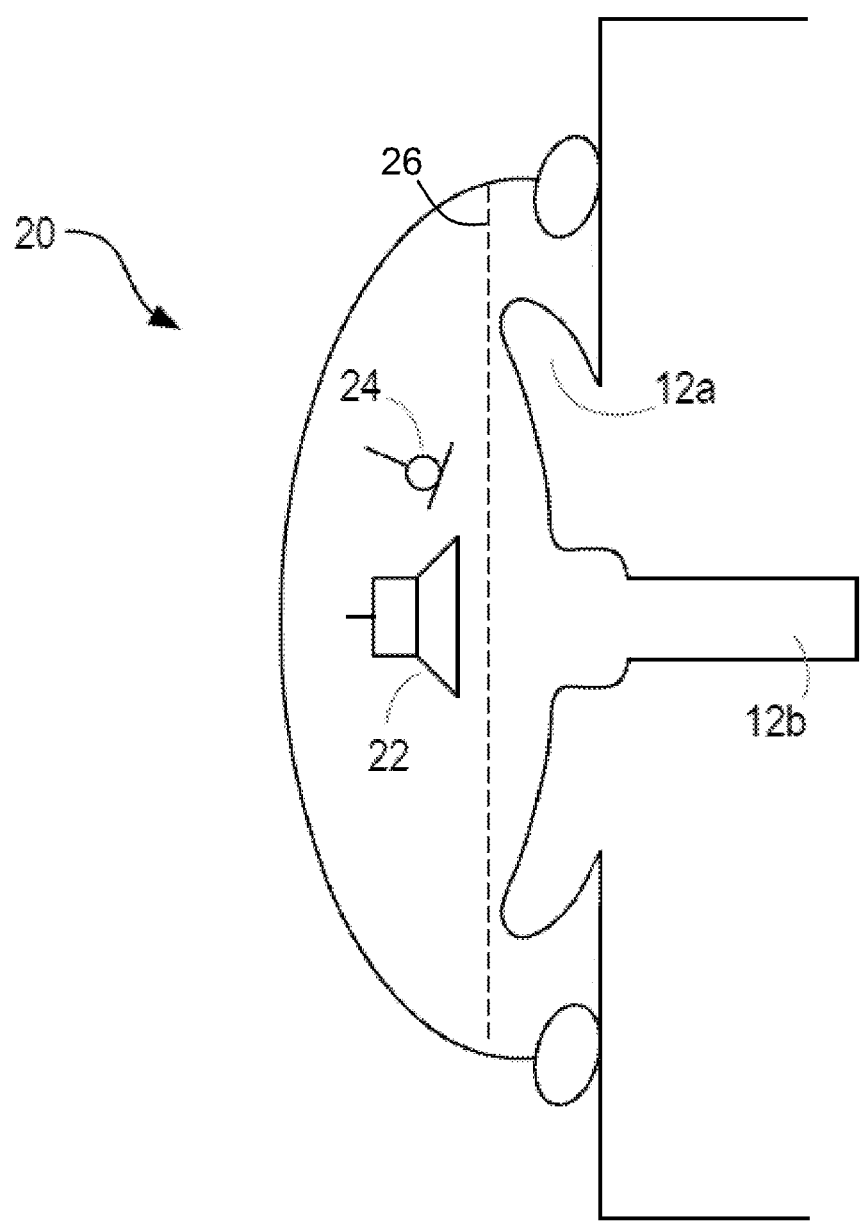
FIGS. 1a to 1e are schematic diagrams of example personal audio devices.

FIG. 1a shows a schematic diagram of a user's ear, comprising the (external) pinna or auricle 12a, and the (internal) ear canal 12b. A personal audio device 20 comprising a circum-aural headphone is worn by the user over the ear. The headphone comprises a shell which substantially surrounds and encloses the auricle 12a, so as to provide a physical barrier between the user's ear and the external environment. Cushioning or padding may be provided at an edge of the shell, so as to increase the comfort of the user, and also the acoustic coupling between the headphone and the user's skin (i.e. to provide a more effective barrier between the external environment and the user's ear).

The headphone comprises one or more loudspeakers 22 positioned on an internal surface of the headphone, and arranged to generate acoustic signals towards the user's ear and particularly the ear canal 12b. The headphone further comprises one or more microphones 24, also positioned on the internal surface of the headphone, arranged to detect acoustic signals within the internal volume defined by the headphone, the auricle 12a and the ear canal 12b. The headphone further comprises a grille 26 between the speaker 22 and the ear which may allow sound to pass but prevents ingress of dirt, moisture and other matter that may cause damage to components of the headphone.

The headphone may be able to perform active noise cancellation, to reduce the amount of noise experienced by the user of the headphone. Active noise cancellation operates by detecting a noise (i.e. with a microphone), and generating a signal (i.e. with a loudspeaker) that has the same amplitude as the noise signal but is opposite in phase. The generated signal thus interferes destructively with the noise and so lessens the noise experienced by the user. Active noise cancellation may operate on the basis of feedback signals, feedforward signals, or a combination of both. Feedforward active noise cancellation utilizes one or more microphones on an external surface of the headphone, operative to detect the environmental noise before it reaches the user's ear. The detected noise is processed quickly, and the cancellation signal generated so as to match the incoming noise as it arrives at the user's ear. Feedback active noise cancellation utilizes one or more error microphones positioned on the internal surface of the headphone, operative to detect the combination of the noise and the audio playback signal generated by the one or more loudspeakers. This combination is used in a feedback loop, together with knowledge of the audio playback signal, to adjust the cancelling signal generated by the loudspeaker and so reduce the noise. The microphone 24 shown in FIG. 1a may therefore form part of an active noise cancellation system, for example, as an error microphone.

Figure 1B:
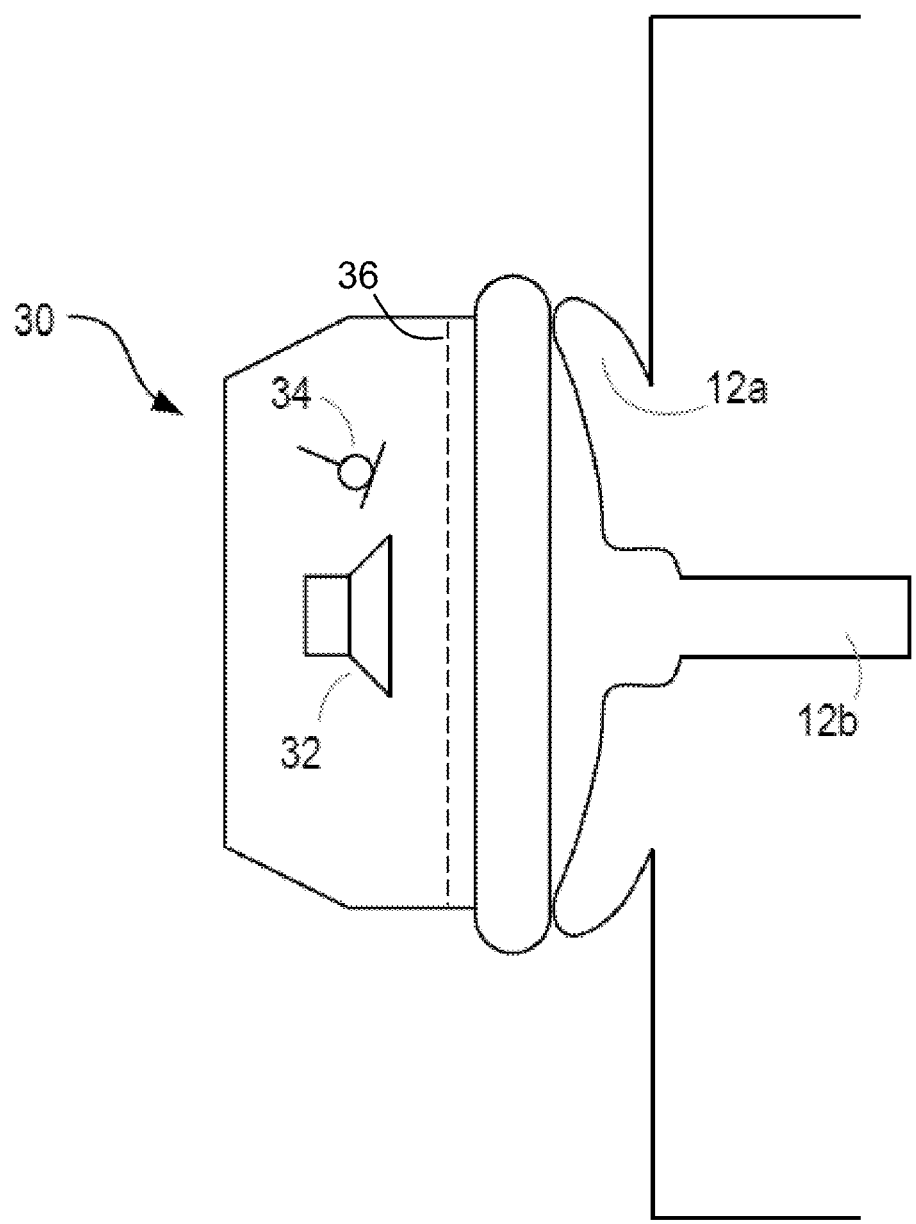

FIG. 1b shows an alternative personal audio device 30, comprising a supra-aural headphone. The supra-aural headphone does not surround or enclose the user's ear, but rather sits on the auricle 12a. The headphone may comprise a cushion or padding to lessen the impact of environmental noise. As with the circum-aural headphone shown in FIG. 1a, the supra-aural headphone comprises one or more loudspeakers 32, one or more microphones 34, and one or more grilles 36. The loudspeaker(s) 32 and the microphone(s) 34 may form part of an active noise cancellation system, with the microphone 34 serving as an error microphone.

Figure 1C:
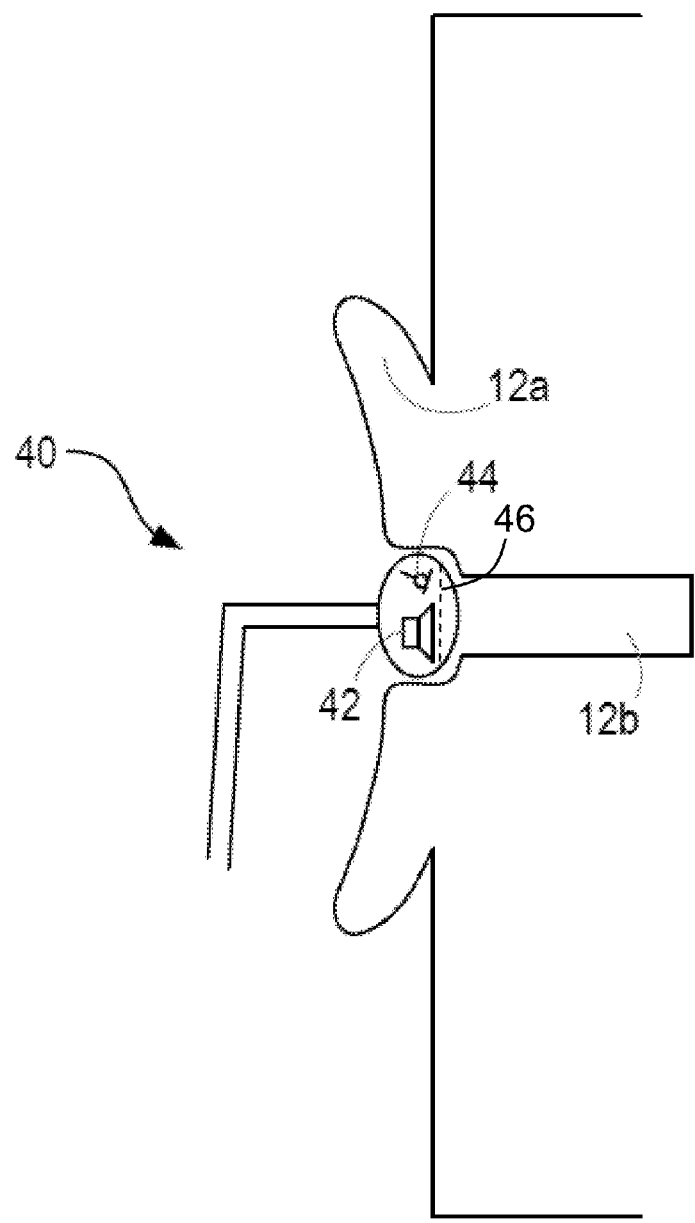

FIG. 1c shows a further alternative personal audio device 40, comprising an intra-concha headphone (or earphone). In use, the intra-concha headphone sits inside the user's concha cavity. The intra-concha headphone may fit loosely within the cavity, allowing the flow of air into and out of the user's ear canal 12*b*.

As with the devices shown in FIGS. 1*a* and 1*b*, the intra-concha headphone comprises one or more loudspeakers 42 and one or more microphones 44, which may form part of an active noise cancellation system, together with one or more grilles 46.

Figure 1D:
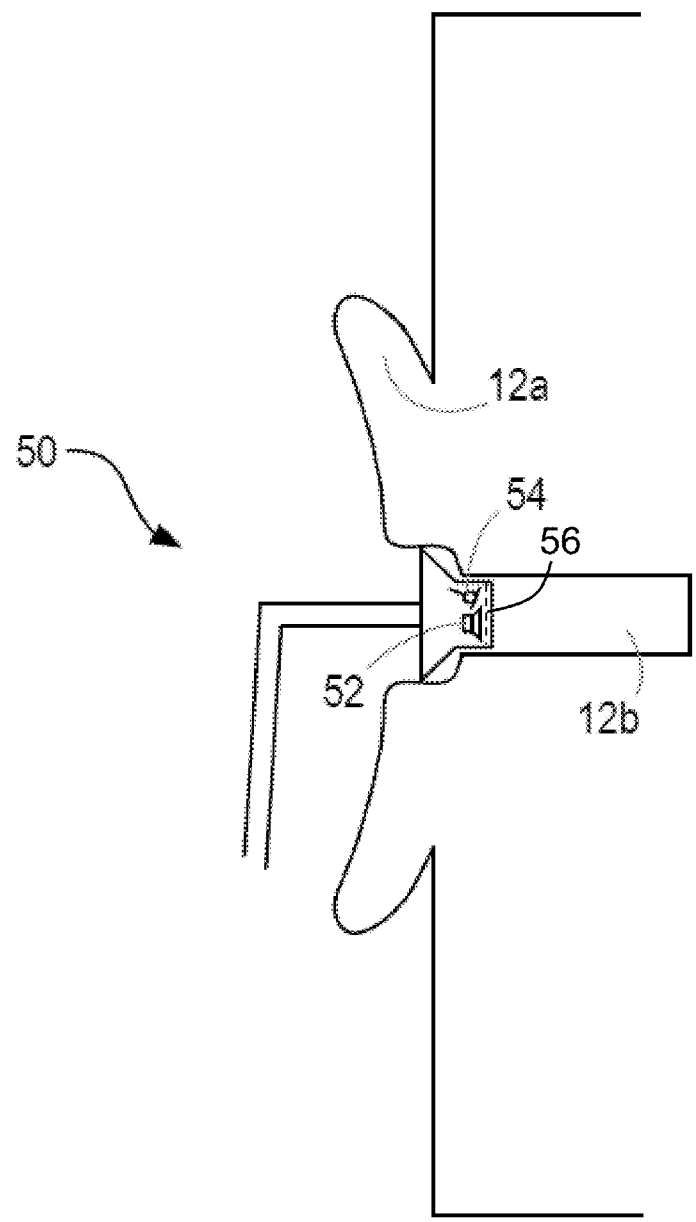

FIG. 1*d* shows a further alternative personal audio device 50, comprising an in-ear headphone (or earphone), insert headphone, or ear bud. This headphone is configured to be partially or totally inserted within the ear canal 12*b*, and may provide a relatively tight seal between the ear canal 12*b* and the external environment (i.e. it may be acoustically closed or sealed). The headphone may comprise one or more loudspeakers 52, one or more microphones 54, and one or more grilles 56, as with the others devices described above, and these components may form part of an active noise cancellation system.

As the in-ear headphone may provide a relatively tight acoustic seal around the ear canal 12*b*, external noise (i.e. coming from the environment outside) detected by the microphone 54 is likely to be low.

Figure 1E:
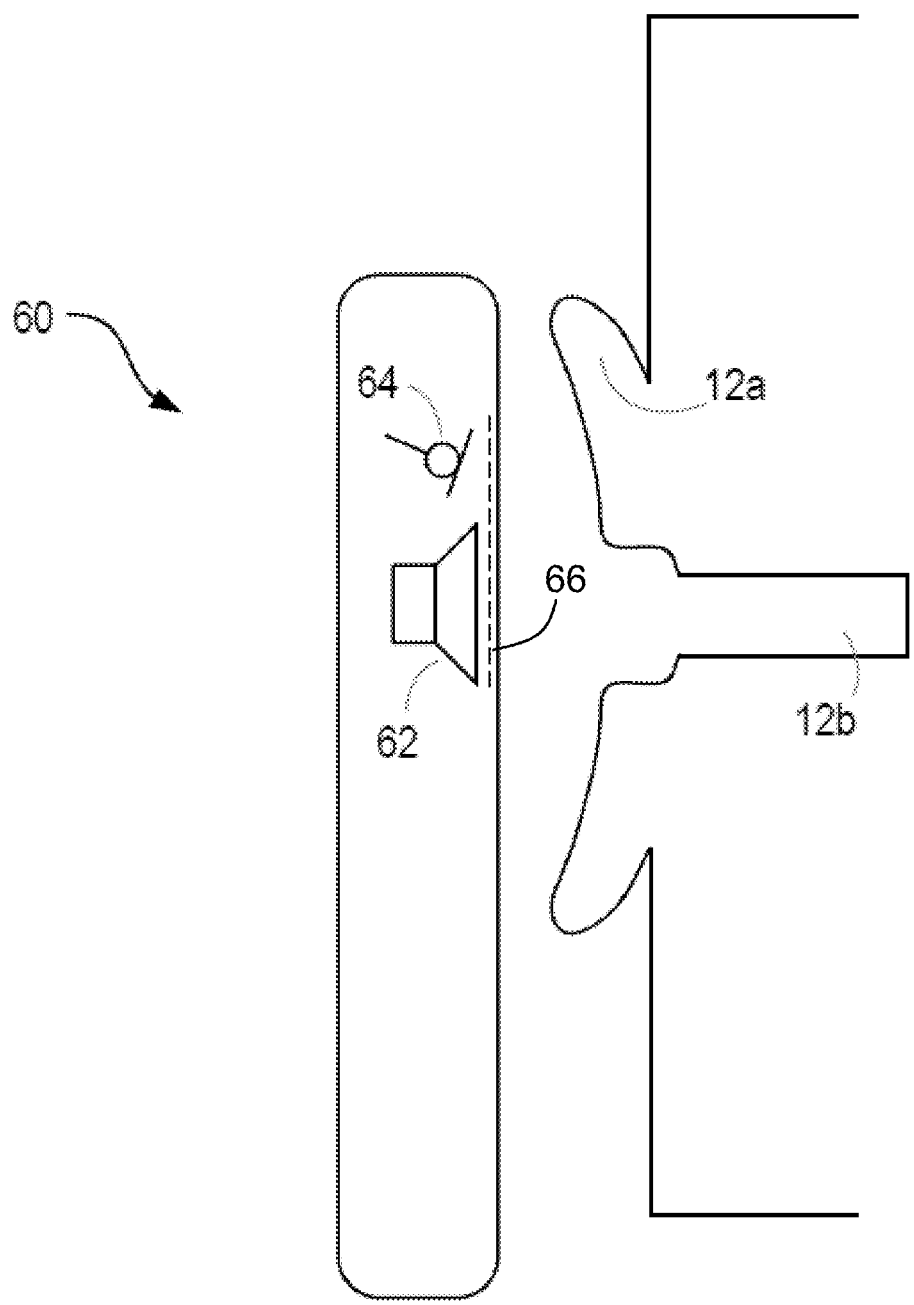

FIG. 1*e* shows a further alternative personal audio device 60, which is a mobile or cellular phone or handset. The handset 60 comprises one or more loudspeakers 62 for audio playback to the user, and one or more microphones 64 which are similarly positioned, together with one or more grilles 66 for allowing sound to pass into and out of the device 60 whilst preventing ingress of grit, dirt, moisture and other matter which may cause damage to internal components of the device 60.

In use, the handset 60 is held close to the user's ear so as to provide audio playback (e.g. during a call). While a tight acoustic seal is not achieved between the handset 60 and the user's ear, the handset 60 is typically held close enough that an acoustic stimulus applied to the ear via the one or more loudspeakers 62 generates a response from the ear which can be detected by the one or more microphones 64. As with the other devices, the loudspeaker(s) 62 and microphone(s) 64 may form part of an active noise cancellation system.

All of the personal audio devices described above thus provide audio playback to substantially a single user in use. Each device comprises one or more loudspeakers and one or more microphones, which may be utilized to generate diagnostic data related to the frequency response of an environment within which the device is located. The loudspeaker is operable to generate an acoustic stimulus, or acoustic probing wave, within the enclosure, and the microphone is operable to detect and measure a response to the acoustic stimulus, e.g. to measure acoustic waves reflected from the surface of the enclosure. The acoustic stimulus may be sonic (for example in the audio frequency range of say 20 Hz to 20 kHz) or ultra-sonic (for example greater than 20 kHz or in the range 20 kHz to 50 kHz) or near-ultrasonic (for example in the range 15 kHz to 25 kHz) in frequency. The acoustic stimulus may have frequency components which span one or more of sonic, ultra-sonic, and near-ultrasonic ranges. In some examples the microphone signal may be processed to measure received signals of the same frequency as that transmitted.

Each of the personal audio devices described above comprises one or more loudspeakers in addition to one or more microphones. However, in some embodiments, the one or more speakers may be used both to generate an acoustic stimulus and as an input device to detect and measure a response to the acoustic stimulus, e.g. to measure acoustic waves reflected from the enclosure. For example, the response may be estimated by measuring the current through the loudspeaker or transducer. Alternatively, for example, the response may be estimated by calculating the impedance of the loudspeaker or transducer. In such cases, the one or more microphones may be omitted.

Figure 2A:
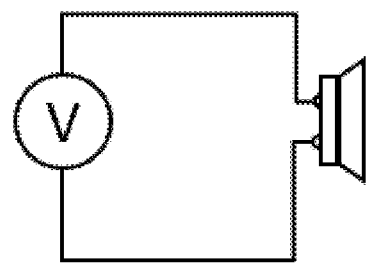
FIG. 2a is an example circuit for generating sound from a speaker.
Figure 2B:
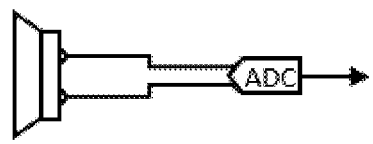
FIG. 2b is an example circuit for deriving a response to an acoustic stimulus from a speaker when the speaker is not being used to generate an acoustic stimulus.
Figure 2C:
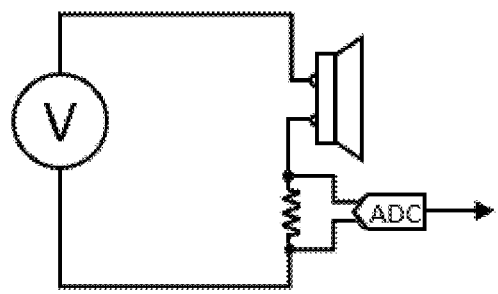
FIG. 2c is an example circuit for deriving a response to an acoustic stimulus from a speaker when the speaker is being used to generate an acoustic stimulus.

Referring to FIG. 2*a*, there is shown an example circuit for generating sound from a speaker 62. FIG. 2*b* is an example circuit for deriving a response to an acoustic stimulus from a speaker 62 when the speaker is not being used to generate the acoustic stimulus i.e., characterising the speaker when the speaker is not being driven. FIG. 2*c* is an example circuit for deriving a response to an acoustic stimulus from a speaker 62 when the speaker is being used to generate the acoustic stimulus i.e., characterising the speaker when the speaker is being driven. For example, the response is derived from a determination of the speaker current, which is estimated by measuring a voltage drip across a known resistor.

All of the devices shown in FIGS. 1*a* to 1*e* and described above may be used to implement aspects of the disclosure.

Figure 3:
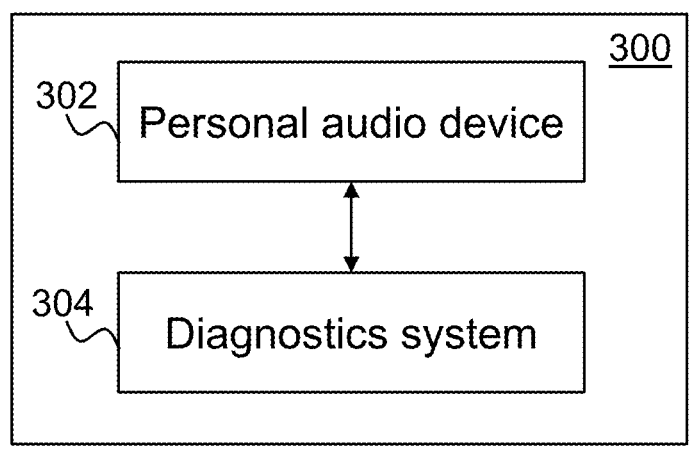
FIG. 3 is a block diagram of an arrangement, according to embodiments of the present disclosure.

FIG. 3 shows an arrangement 300 according to embodiments of the disclosure. The arrangement 300 comprises a personal audio device 302 and a diagnostic system 304. The personal audio device 302 may be any device which is suitable for, or configurable to provide audio playback to substantially a single user. The personal audio device 302 generally comprises one or more loudspeakers, and one or more microphones which, in use, are positioned adjacent to or within a user's ear. The personal audio device 302 may be wearable, and comprise a headset or headphones for each of the user's ears. Alternatively, the personal audio device 302 may be operable to be carried by the user, and held adjacent to the user's ear or ears during use. The personal audio device 302 may comprise headphones or a mobile phone handset, as described above with respect to any of FIGS. 1*a* to 1*e*.

The diagnostic system 304 is coupled to the personal audio device 302 and operative to control the personal audio device 302 to acquire diagnostic data which is indicative of the condition of one or more components of the personal audio device 302.

As mentioned previously, a problem associated with personal audio devices, such as headsets, is the susceptibility of a measured response to change over time due to deterioration of one or more components of the device used for detecting the response. For example, deterioration of the speakers and/or microphones or ingress of dirt in the speaker grille of a headphone, such as those shown in FIGS. 1*a* to 1*e*, can lead to a change in the characteristics of sound output from the headphone as well as signals received at an internal microphone in the headphone.

The personal audio device 302 generates an acoustic stimulus to be played from a loudspeaker of the personal audio device 302, and detects or measures the response to the acoustic stimulus. The measured response corresponds to the reflected signal received at the one or more transducers, with certain frequencies being reflected at higher amplitudes than other frequencies owing to the particular response of the environment within which the personal audio device 302 or headset of the personal audio device 302 is located, such as an acoustic enclosure (e.g., a charging case for one of the personal audio devices 20, 30, 40, 50, 60 described above with reference to FIGS. 1*a* and 1*e*).

The diagnostic system 304 may send suitable control signals to the personal audio device 302, so as to initiate the acquisition of diagnostic data, and receive data from the personal audio device 302 corresponding to the measured response. The diagnostic system 304 is operable to extract one or more features from the measured response and utilize those features as part of a diagnostic process.

By comparing the measured response to a stored template of expected response, such as that pre-programmed into the personal audio devices during manufacture or during a post manufacture calibration procedure, the diagnostic system 304 can determine if the personal audio devices has become impaired or has degraded in some way. In some embodiments, the diagnostic system 304 is configured to determine which of the components (e.g., speaker(s) and/or microphone(s) and/or grille) of the personal audio device 302 are impaired. The diagnostic system 304 may periodically perform a diagnostic process and maintain a record of deterioration of components of the personal audio device over time. This record may be used to predict when repair or replacement of components of the personal audio device may be required, for example. This record may also provide valuable insight into the aging process of the components.

The diagnostic system 304 may, in some embodiments, form part of the personal audio device 302 itself. Alternatively, the diagnostic system 304 may form part of an electronic host device (e.g. an audio player) or the acoustic enclosure to which the personal audio device 302 is coupled, through wires or wirelessly. In yet further embodiments, operations of the diagnostic system 304 may be distributed between circuitry in the personal audio device 302, the electronic host device and/or the acoustic enclosure.

Figure 4:
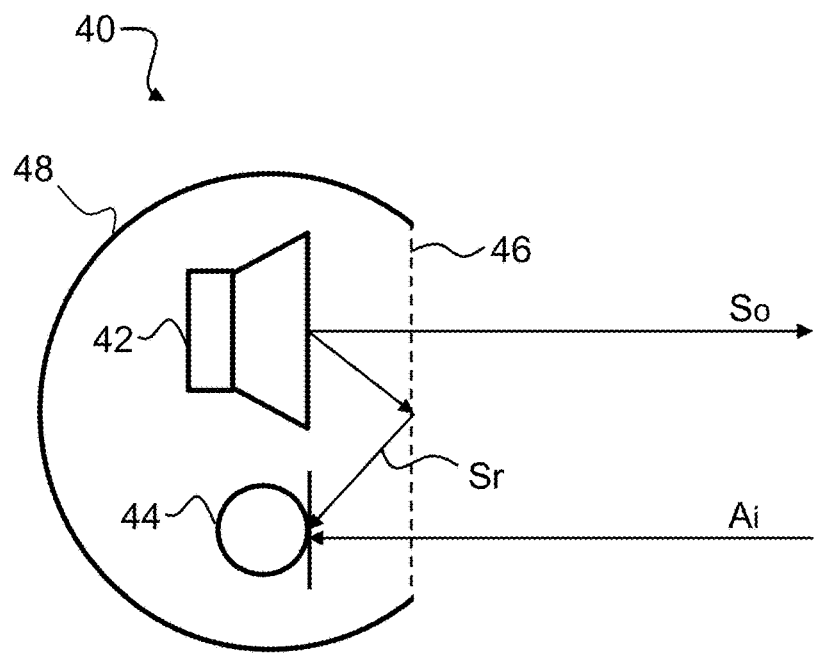
FIG. 4 is a block diagram of a personal audio device, according to embodiments of the present disclosure.

FIG. 4 is a more detailed schematic diagram of the personal audio device 40 described above. The following explanation is described with reference to the personal audio device 40, but equally applies to any of the personal audio devices described above or herein which each comprise components which may be susceptible to deterioration.

The device 40 comprises a loudspeaker 44 and a first microphone 42 housed within a headphone shell 48. A grille 46 is provided in the headphone shell 48 and configured to allow sound to pass therethrough while preventing or mitigating ingress of dirt, moisture and the like into the shell 48. Arrows $S_o$ represents a component of sound originating from the speaker 42 which is transmitted through the grille 48 to the outside of the audio device 40. Arrow $S_r$ represents a component of sound generated by the speaker 42 which is reflected from the inside surface of the grille 46 and is incident at the microphone 44. Arrow Ai represents the component of ambient sound outside of the shell 48 transmitted through the grille 46 which is incident at the microphone 44.

As foreign matter (dirt, wax, skin etc.) builds up on and in the grille 46, the energy of components So, Ai of sound transmitted through the grille 46 and reaching the microphone 44 decrease due to increased absorption at the grille 46. Additionally, the energy of the component Sr reflected at the internal surface of the grille 46 may increase.

Figure 5:
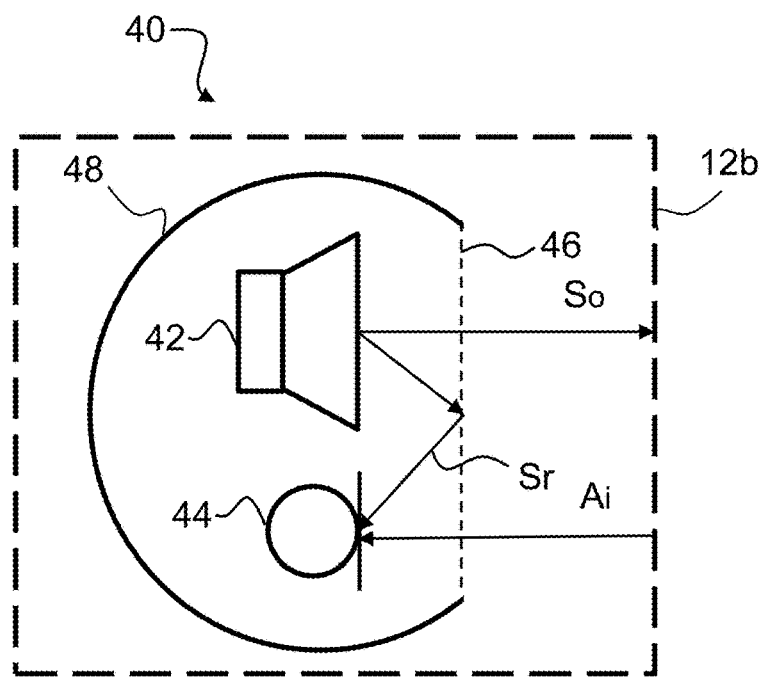
FIG. 5 is a block diagram of the personal audio device of FIG. 3 positioned within an acoustic enclosure, according to embodiments of the present disclosure.

FIG. 5 shows the device 40 positioned within the acoustic enclosure 12b, such as the charging case. Again, it will be appreciated that, with ingress of dirt and other matter in the grille 46, a measured response of the acoustic enclosure at the microphone 44 to an acoustic stimulus output at the speaker 42 may change over time.

Similarly, degradation of the speaker 42 and/or microphone 44 may result in a measured response of the acoustic enclosure at the microphone 44 to an acoustic stimulus output at the speaker 42 changing over time. Also, damage to the speaker 42 and/or microphone 44 may result in a measured response of the acoustic enclosure at the microphone 44 to an acoustic stimulus output at the speaker 42 changing from its original measured response, as may have been programmed into the personal audio device 202 during manufacture or during a post manufacture calibration procedure.

Figure 6:
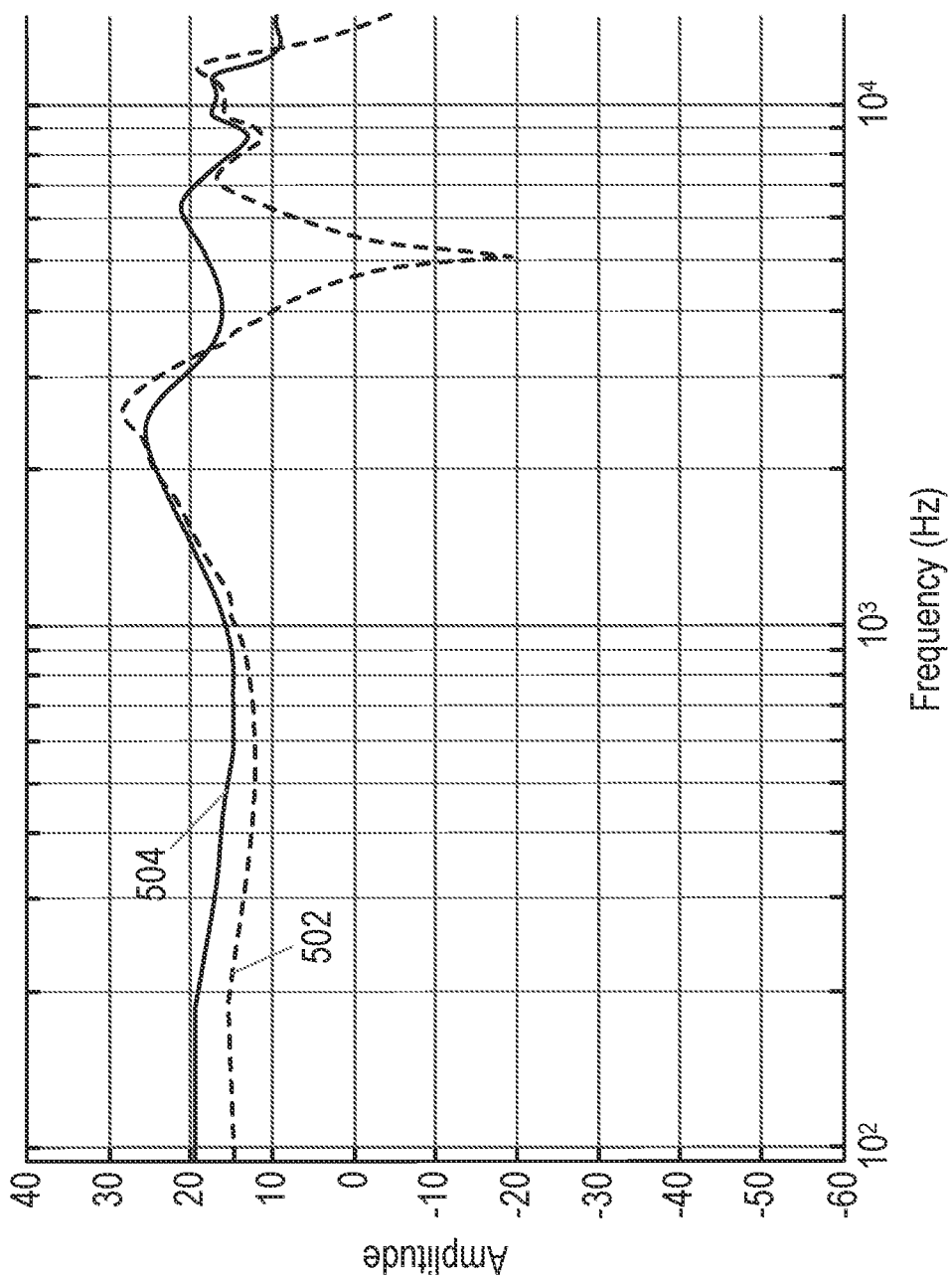
FIG. 6 is graph illustrating frequency responses of a microphone to white noise output at a speaker in the presence of a clean grille and a dirty grille.

FIG. 6 graphically illustrates the frequency responses 402, 404 of the microphone 44 to white noise output at the speaker 42 in the presence of a clean grille 46 (line 502) and a dirty grille 46 (line 504) with the device 40 positioned at the ear canal 12b. Referring first to line 502, it can be seen that a large "notch" (reduction in amplitude) can be seen between about 3 kHz and about 7 kHz in the signal received at the microphone 44. This "notch" is dependent on the characteristics of the ear canal 12b or external acoustic path and thus can be used as an feature in ear biometrics. Referring then to line 504 in comparison, a comparative increase in amplitude of the response 404 can be seen between about 3 kHz and about 7 kHz with ingress of dirt and was on and in the grille 46. This increase in amplitude is caused by an increase in reflection of sound from the internal surface of the grille due to the deteriorating condition. Referring to FIG. 5, the change in the reflected component Sr accounts for this noise which substantially removes the notch at the detriment of biometric processes. Thus, a change in condition of the grille 46 can substantially affect a measured response detected at the microphone 44.

Accordingly, when the personal audio device 302 is enclosed in a known acoustic enclosure, by comparing a detected response with an expected response (or characteristics thereof), a diagnosis of the condition of components (e.g., the speaker(s), microphone(s) and/or grilles) of the personal audio device 302 can be made.

In view of the above, embodiments of the present disclosure provide methods and systems for diagnosing or determining conditions of components of personal audio devices by determining one or more characteristics of signals received at a transducer of such devices in response to an acoustic stimulus. For example, embodiments of the present disclosure may output an acoustic stimulus from a speaker and measure a response signal at a transducer, such as the speaker and/or a microphone. The response signals and/or one or more characteristics thereof may then be analysed to diagnose the transducer (speaker and/or microphone) as being impaired or not impaired.

Furthermore, in some embodiments, a condition of elements in the acoustic path of the device, such as a condition of a grille, may be determined. Examples of the elements include, but are not limited to physical elements such as a speaker grille or cover, an acoustic port, an acoustic channel and the like. Examples of a condition of such elements include, but are not limited to a level of build-up or ingress of dirt or wax or any other matter which may attenuate sound travelling to and from the transducer(s).

In some embodiments, diagnosis of the transducer(s) is based on a comparison of the response signals (and/or one or more characteristics thereof) of the transducer(s) to a template of a response signals (and/or one or more characteristics thereof) for that transducer(s). A template response signal may be determined for each transducer pair of the personal audio device, and/or a pair of personal audio devices. For example, an acoustic signal may be generated by a first speaker of a first device and a template signal response may be recorded for each of: the first speaker of the first personal device, first, second and further (if appropriate) microphones of the first personal device, second speaker of a second personal device, and first, second and further (if appropriate) microphones of the second personal device.

For example, a template for each transducer may be pre-programmed into the personal audio devices during manufacture or during a post manufacture calibration procedure. In some embodiments, the personal audio devices is configured to perform an initialisation calibration procedure once the personal audio device has been manufactured and is placed in the enclosure, e.g., charging case. During this initialisation calibration procedure, acoustic signals are output from each speaker of the personal audio device, responses are derived from each transducer (including the speaker and/or any microphones) of the personal audio device 302 and templates for each transducer are generated to store the response signal (and/or one or more characteristics thereof) for that transducer at initialisation. Advantageously, such initialisation calibration procedure mean that the templates generated for each transducer are specific to those transducers. This is in contrast to alternative calibration processes where generic templates for each type of transducer (speaker, internal microphone, external microphone etc.) are pre-programmed into the personal audio devices during manufacture.

Based on the diagnosis, one or more sound enhancement processes may be performed, adjusted or updated in one or more ways to account for the condition or a change in the condition, such as a deterioration of the condition of the component or element causing a change in a measured response to the acoustic stimulus.

In the case of a speaker that has an altered sensitivity or frequency response (for example due to the speaker being impaired or an obstruction in the speaker grille), such processes may include an adjustment of an equalisation filter (not shown) such that the frequency response during music playback or transparency mode that is experienced by the user is maintained. In the case of a microphone that has altered sensitivity or frequency response such processes may include application of calibration offset or filter (not shown) such that the microphone response is corrected prior to use. In the case of an in-ear microphone that is effected by sound generated by the speaker reflecting back from an obstructed speaker grille, such processes may include the derivation of a cancelation filter (not shown) which removes the signals created by such reflections.

Diagnosis may be performed periodically and a record of the "health" of the personal audio device 302 maintained. In this way, deterioration in the components of the personal audio device 302 may be detected early and appropriate action taken, such as instigating repair or replacement of the deteriorated component. Periodical diagnosis may also allow for trends in the health of the personal audio device 302, and in some instances, the health of the user of the personal audio device to be monitored. For example, a relatively rapid build-up of wax in the grille may be an indicator that the user has an infectious disease, such as external otitis (swimmer's ear). In some embodiments, diagnostic data may be transmitted from the personal audio device 302 and/or diagnostic system 304 to a remote server for storage.

Figure 7:
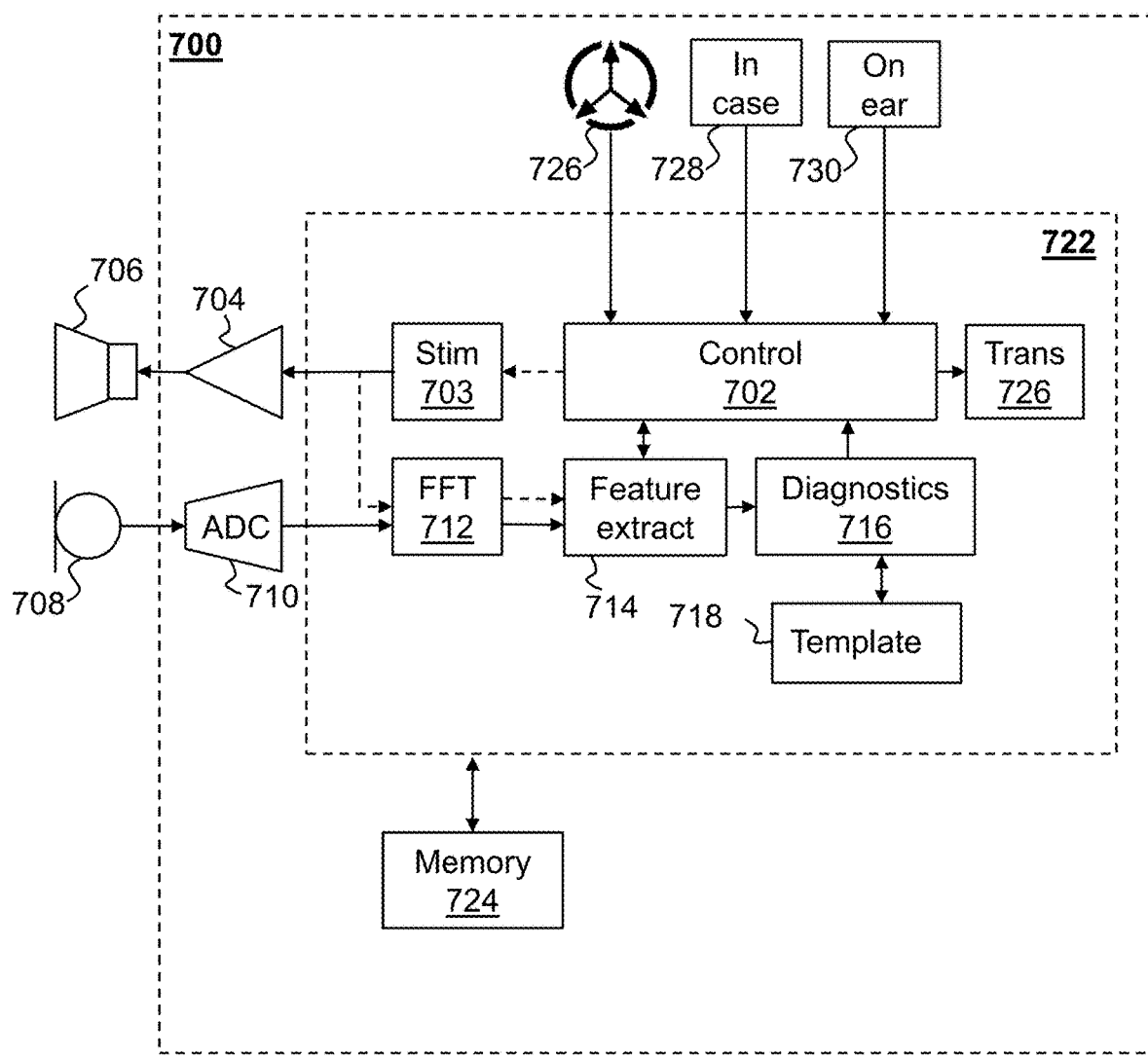
FIG. 7 is a schematic of a system, according to embodiments of the present disclosure.

FIG. 7 shows a system 700 according to embodiments of the disclosure.

The system 700 comprises processing circuitry 722, which may comprise one or more processors, such as a central processing unit or an applications processor (AP), or a digital signal processor (DSP).

The one or more processors may perform methods as described herein on the basis of data and program instructions stored in memory 724. Memory 724 may be provided as a single component or as multiple components or co-integrated with at least some of processing circuitry 722. Specifically, the methods described herein may be performed in processing circuitry 722 by executing instructions that are stored in non-transient form in the memory 724, with the program instructions being stored either during manufacture of the system 700 or personal audio device 302 or by upload while the system 700 or device 702 is in use.

The processing circuitry 722 comprises a stimulus generator module 703 which is coupled directly or indirectly to an amplifier 704, which in turn is coupled to a transducer 706. The transducer 706 and a microphone 708 may form part of a personal audio device, such as the personal audio devices 20, 30, 40, 50, 60 described above with reference to FIGS. 1a to 1e. In other embodiments the transducer 706 may act both as a speaker for generating sound and a microphone or inductor for generating signals from sound incident thereon.

The stimulus generator module 703 generates an electrical audio signal and provides the electrical audio signal to the amplifier 704, which amplifies it and provides the amplified signal to the transducer 706. The transducer 706 generates a corresponding acoustic signal which is output to the user's ear (or ears). In alternative embodiments, the amplifier 704 may form part of the stimulus generator module 703.

As noted above, when the transducer 706 and microphone 708 are positioned at an ear entrance of the user, the audio signal may be output to all or a part of the user's ear (i.e. the auricle 12a or the ear canal 12b of the user as described with reference to FIGS. 1a to 1e). The audio signal is reflected off the ear, and the reflected signal (or echo signal) is detected and received by the microphone 708. The reflected signal thus comprises data which is characteristic of the individual's ear, and suitable for use as a biometric. When the transducer 706 and the microphone 708 are positioned, instead of at the ear, in an acoustic enclosure such as a charging case for one of the personal audio devices 20, 30, 40, 50, 60 described above with reference to FIGS. 1a and 1e, the audio signal is reflected off the internal walls and features of the acoustic enclosure and such reflections may thus comprise data which is characteristic of the enclosure. When the transducer 706 and the microphone 708 are positioned, instead of at the ear or in an acoustic enclosure, in free field, i.e. positioned on a table or other surface in the open, there are no physical barriers for the audio signal to be reflected off outside of the device. An absence of reflected sound incident at the microphone 708 is characteristic of this free field condition.

In any of the above scenarios (ear, enclosure or free field), in addition to any reflections either from the ear or from features of an acoustic enclosure, the audio signal may also be reflected off features internal to the device in which the transducer 706 is positioned. Such features may include obstacles (e.g. a speaker grille) in the acoustic path of the transducer. As such, reflected components of the signal may comprise data which is characteristic of these obstacles (e.g. a condition of the speaker grille etc.).

If the acoustic environment in which the transducer 706 and microphone 708 resides is known, characteristics of the signal received at the microphone 708 when the transducer 706 and microphone 708 are performing optimally or to an expected standard can be determined and stored as a template as discussed above. Accordingly, if characteristics of the signal received at the microphone 708 differ from the expected characteristics, for example, by greater than a threshold amount, it can be deduced that the microphone 708 and/or the transducer 706 is impaired and/or there is an obstacle, such as a dirty grille, that is impacting the response signal characteristics. Furthermore, the condition of any obstacles in the acoustic path of the transducer can be estimated based on characteristics of the signal received at the microphone 708.

The reflected signal is passed from the microphone 708 to an analogue-to-digital converter (ADC) 710, where it is converted from the analogue domain to the digital domain. In alternative embodiments the microphone 708 may be a digital microphone and produce a digital data signal (which does not therefore require conversion to the digital domain).

The signal is detected by the microphone 708 in the time domain. However, the features extracted for the purposes of diagnostics processing and condition estimation may be in the frequency domain (in that it is the frequency response of the enclosure, or the obstacles which is generally characteristic). In which case, the system 700 may comprise a Fourier transform module 712, which converts the reflected signal to the frequency domain. For example, the Fourier transform module 712 may implement a fast Fourier transform (FFT).

The transformed signal is then passed to a feature extract module 714, which extracts one or more features of the transformed signal for use in a diagnostics process and/or a condition determination process. For example, the feature extract module 714 may extract the resonant frequency of the acoustic enclosure in which the transducer is located. For example, the feature extract module 714 may extract one or more mel frequency cepstral coefficients. Alternatively, the feature extract module 714 may determine a frequency response at one or more predetermined frequencies, or across one or more ranges of frequencies. The frequency response may be of an acoustic enclosure (e.g. charging case), or of free field in combination with the internals of a headphone shell. To extract such features, the acoustic stimulus generated at the stimulus generator module 703 is also provided to the feature extract module 714, optionally via the Fourier transform module 712, depending on whether the stimulus generator module 703 outputs the acoustic stimulus in the time or frequency domain. By providing the acoustic stimulus to the feature extract module 714, a comparison can be made between the acoustic stimulus and the response to that acoustic stimulus received at the microphone 708.

For characterisation of the condition of elements in the acoustic path of the transducer 706 and microphone 708, the feature extract module 714 may calculate an impedance or reflectance of one or more features in the acoustic path, such as a speaker grille.

To aid the feature extraction module 714 in determining the various extracted features discussed above, the system 700 may further comprise an accelerometer 726 comprised in or associated with a headphone into which the transducer 706 and the microphone 708 are incorporated. The control module 702 may receive one or more inputs from the accelerometer 726 which may in turn be used to determine an orientation of the headphone which may correspond to the headphone being placed on a surface in free field. The control module 702 may further comprise one or both of an in-case detect module 728 and an on-ear detect module 730. The in-case detect module 728 may be configured to detect that the personal audio device 202 into which transducer 706 and microphone 708 are incorporated is housed with an associated acoustic enclosure, such as a charging case. The on-ear detect module 730 may be configured to detect when or whether the personal audio device 202, in particular the transducer 706 is inserted in or located in proximity to the ear. The control module 702 may receive as inputs indications of a free-field condition, an in-case condition or an on-ear condition and provide these to the feature extract module 714. In turn, the feature extract module 714 may extract one or more features based on the environment within which the transducer 706 and microphone 708 are positioned. In some embodiments, the diagnostic process will only be performed if the control module 702 receives an input from the in-case detect module 728 indicating that the personal audio device 202 into which transducer 706 and microphone 708 are incorporated is housed within an associated acoustic enclosure, such as a charging case.

Where the personal audio device 202 comprises multiple microphones, for example additional microphone(s) other than the microphone 708 shown in FIG. 7, signals derived from those additional microphone(s) may be provided to the feature extract module 714 in a similar manner to that described with reference to the microphone 708 shown in FIG. 7. Such derived signal(s) may be used as a reference signal(s), for example to detect excessive noise and/or to assist in feature extraction, diagnostic processes and/or condition detection, particularly if an acoustic path exists between the microphone 708 and the additional microphone(s).

In some embodiments, multiple personal audio devices 202 are provided within the same acoustic enclosure and are capable of communicating with one another. In such cases, signals derived from speaker(s) and/or microphone(s) of a second personal audio device 202 in response to an acoustic stimulus from a speaker of a first personal audio device 202 or from a speaker of the second personal audio device 202 may be used to improve the diagnostic process. For example, the first personal audio device 202 may be configured to receive measured responses, or characteristics thereof, from the second personal audio device 202 via transceiver 726 of the processing circuitry 722. In some embodiments, the acoustic enclosure may comprise processing circuitry (not shown) configured to receive measured responses, or characteristics thereof, from the first and/or second personal audio device 202 and to perform the diagnosis process.

In some embodiments, such an acoustic enclosure may comprise a body disposed within the enclosure, wherein a first recess disposed in the body and arranged to receive a first earphone comprising a first speaker and a second recess disposed in the body and arranged to receive a second earphone comprising a second speaker. The body may be configured such that the first speaker is orientated towards the second speaker when the first and second earphone are received by the respective first and second recesses. In this way, improved acoustic coupling between the first and second earphones may be achieved and the second earphone may provide for redundancy in diagnostic testing of the first earphone.

Extracted feature(s) pertaining to diagnostics may be passed to a diagnostics module 716, which performs a diagnostics process on them. For example, the diagnostics module 716 may determine whether or not components of the personal audio devices 202 are impaired or have deteriorated over a period of time or whether there is an obstacle in the acoustic path. The diagnostics module 716 may compare extracted features from the measured response signal to corresponding features of a stored template 718 of expected features for that component. The diagnostics module 716 generates a diagnostic result (which may be the indication of the impairment or non-impairment of one or more components of the personal audio device, or a measure of the deterioration of the one or more components over a time period, or the indication of an obstacle in the acoustic path) and outputs the result to the control module 702.

The template 718 may store condition data comprising extracted features (or parameters derived therefrom) which are characteristic of the personal audio device 202 in one or more states of condition in one or more known acoustic environments. For example, known acoustic environments may include an acoustic enclosure, such as a charging case. Example states of condition include a new condition or some condition of the personal audio device 40 (and its components) in the past.

To determine a condition of audio device 40, the diagnostics module 716 may compare the one or more extract features to corresponding reference features previously extracted or determined, as stored in template 718. The reference features may have been extracted by the feature extract module 714 during the initialisation calibration procedure as discussed above. Additionally or alternatively, the reference features may be extracted during a baseline calibration measurement made at the time of production or refurbishment of the personal audio device 202. Additionally, or alternatively, the reference features may be features determined during modelling of the personal audio device 202 or otherwise estimated.

The comparison made between the extracted features and reference features may represent a condition of the acoustic path between the transducer 706 and the microphone 708. The comparison made between the extracted features and reference features may represent a condition of the transducer 706 and/or the microphone 708. Based on the comparison, the condition detect module 720 may then determine a condition of one or more components in the acoustic path, such as the speaker grille, the transducer 706 and/or the microphone 708.

In comparing the extracted features and reference features, the diagnostics module 716 may determine a difference between one or more extracted features and a corresponding one or more reference features. If the determined difference exceeds a predetermined threshold, the diagnostics module 716 may output an indication to the control module 702 indicating a deterioration in the condition of the acoustic path and/or the components of the personal audio device 202. Such a deterioration may indicate to the control module 716 that any features extracted by the feature extract module 714 for use in an acoustic enhancement process may be affected by an adverse acoustic condition. In response, the control module 702 may be configured to perform, update, amend, or otherwise change an acoustic enhancement process being undertaken to account for the change in condition of the acoustic path and/or the components of the personal audio device 202.

In addition to or as an alternative to outputting an indication to the control module 702 of an indication of impairment or non-impairment or deterioration in the condition of components and/or the acoustic path, the diagnostics module 716 may output the determined difference or comparison between the one or more extracted features and their corresponding reference features to the control module 702. Such feature difference(s) or comparison(s) may then be used by the control module 702 to cancel noise associated with the deterioration in the condition of the acoustic path. In other words, the determined feature difference(s) may be used to either calibrate the signal derived from the microphone 708 or the features extracted therefrom before such features are used in an acoustic enhancement process. In doing so, noise associated with a deterioration of the condition of the components and/or acoustic path from the ideal may be substantially removed, thus enabling any enhancement process to be substantially unaffected by the noise.

In some embodiments, based on the comparison between extracted and reference features, the control module 702 may be configured to generate one or more parameters of a cancellation filter (not shown) configured to cancel noise associated with the component and/or acoustic path condition deterioration. In some embodiments, the cancellation filter may pre-filter the frequency domain signal output from the Fourier transform module 712 to remove noise associated with the deterioration in the component and/or acoustic path condition. For example, any such filter may be implemented using the feature extract module 714 in the frequency domain. Such a filter may be designed using least mean square filter techniques or other known digital filtering techniques. Any such filtering may be adaptive, such that filter parameters may be updated over time in response to one or more changing conditions of the acoustic path, based on successive comparisons of present extracted features with past or ideal measured or modelled features (reference features). In some embodiments, instead of or in addition to being implemented in the frequency domain, filtration may be implemented in the time domain in a manner known in the art.

Taking the example shown in FIG. 6, such filtering may remove the noise present between 5 kHz and 8 kHz thereby restoring, in the signal derived from the deteriorated acoustic path, the notch present in the frequency response for the clean grille (i.e. the non-deteriorated acoustic path condition).

In some embodiments, a detected change in condition at the diagnostics module 716 may also be used to re-calibrate or adjust one or more parameters of active noise cancellation (ANC). For example, ANC may be switched off altogether (e.g. if a complete blockage of the acoustic path is detected) or a different (e.g. less aggressive) filter may be implemented. For example, where the system 700 implements both feedforward and feedback (FB) ANC, in response to detecting an adverse condition in the acoustic path, FB ANC may be switched off.

In some embodiments, a detected change in condition at the diagnostics module 716 may also be used to adjust one or more characteristics of a personalised equalisation (EQ), e.g. an EQ designed specifically for a user of the personal audio device 202 and the fit of the device 202 to the user's ear.

In some embodiments, a detected change in condition at the diagnostics module 716 may also be used to adjust parameters of any other hearing augmentation, sidetone or other process carried out on any signals being output to the transducer 706.

As discussed previously, the control module 702 may control the stimulus generator module 703 to output an acoustic stimulus specifically for use in a diagnostic process. For example, the control module 702 may be configured to control the stimulus generator module 703 to output a diagnostics cue notifying a user that diagnosis is taking place. The control module 702 may adjust the properties of the acoustic stimulus so as to maximise the SNR of the measured response signal. The control module 702 may, for example, control the stimulus generator module 703 to increase the amplitude of the stimulus output to the transducer 706 or otherwise adjust the frequency response of the signal. In other embodiments, an initial estimate of an enclosure response or speaker grille impedance or reflection, based on the response signal received at the microphone 706 to the initial acoustic stimulus, may first be ascertained.

Then, the control module 702 may control the stimulus generator module 703 to generate an additional acoustic probe signal/stimulus to confirm or strengthen the initial estimate for the purposes of condition detection. The diagnostics module 716 may signal to the control module 702 to adjust and re-apply an acoustic stimulus to the transducer 706 based on a determination in a condition of the acoustic path or a change in such condition over time.

The control module 702 may continue to control the stimulus generator module 703 even while the acoustic stimulus is being applied to the transducer 706. For example, the control module 702 may monitor the extracted features or the response signal itself to determine ongoing properties response signal.

In some embodiments the feature extract module 714 may be designed with foreknowledge of the nature of the stimulus, for example knowing the spectrum of the applied stimulus signal, so that the response or transfer function may be appropriately normalised. In other more suitable embodiments the feature extract module 714 may comprise a second input to monitor the stimulus (e.g. playback music, on-ear detect, a virtual assistant, ANC, hearing augmentation, sidetone, adjusted acoustic stimulus etc.) and hence provide the feature extract module 714 with information about the stimulus signal or its spectrum so that the feature extract module 714 may calculate the transfer function from the acoustic stimulus to measured received signal from the microphone 708 from which it may derive the desired feature parameters. In the latter case, the acoustic stimulus may also pass to the feature extract module 714 via the FFT module 712 (denoted by dotted line in FIG. 7).

Figure 8A:
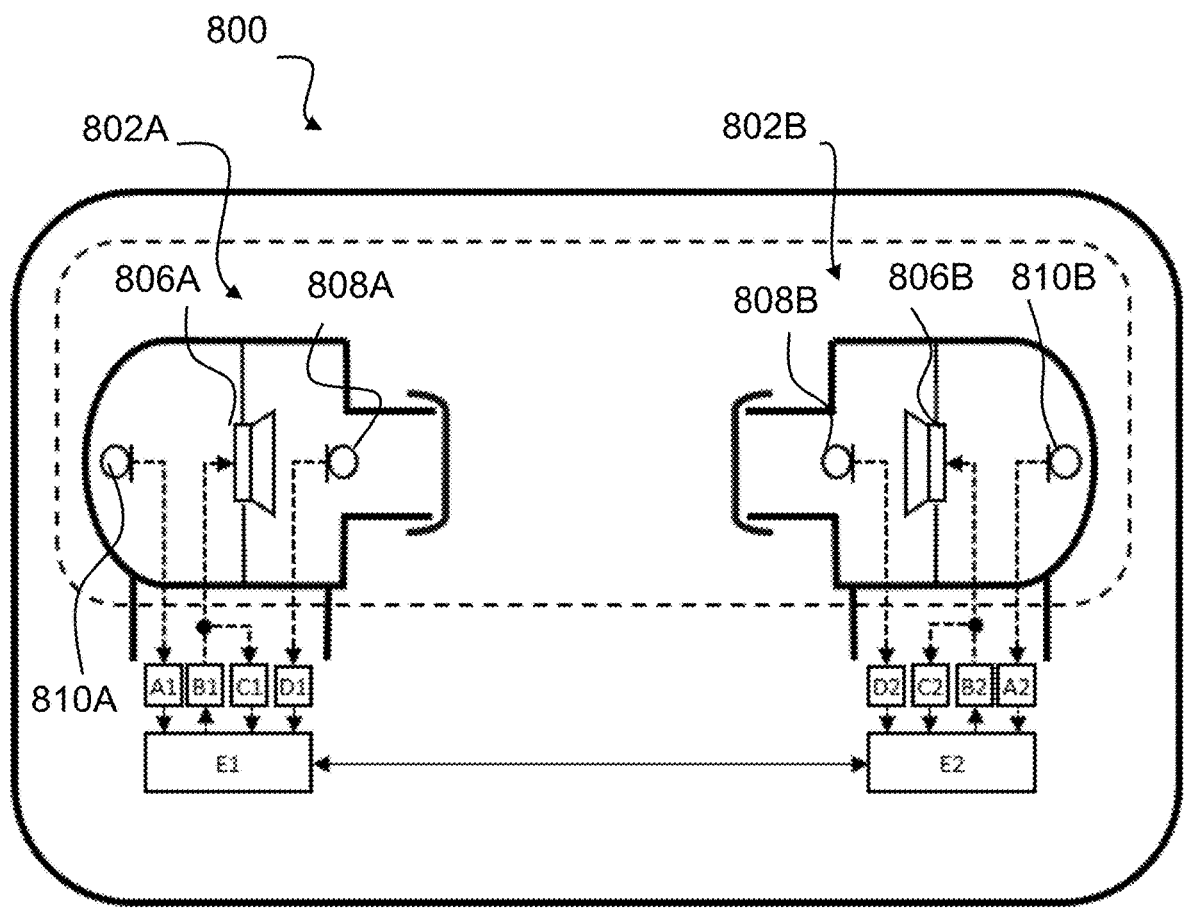
FIGS. 8A, 8B and 8C are schematics of an enclosure comprising first and second headsets, according to embodiments of the present disclosure.
Figure 8B:
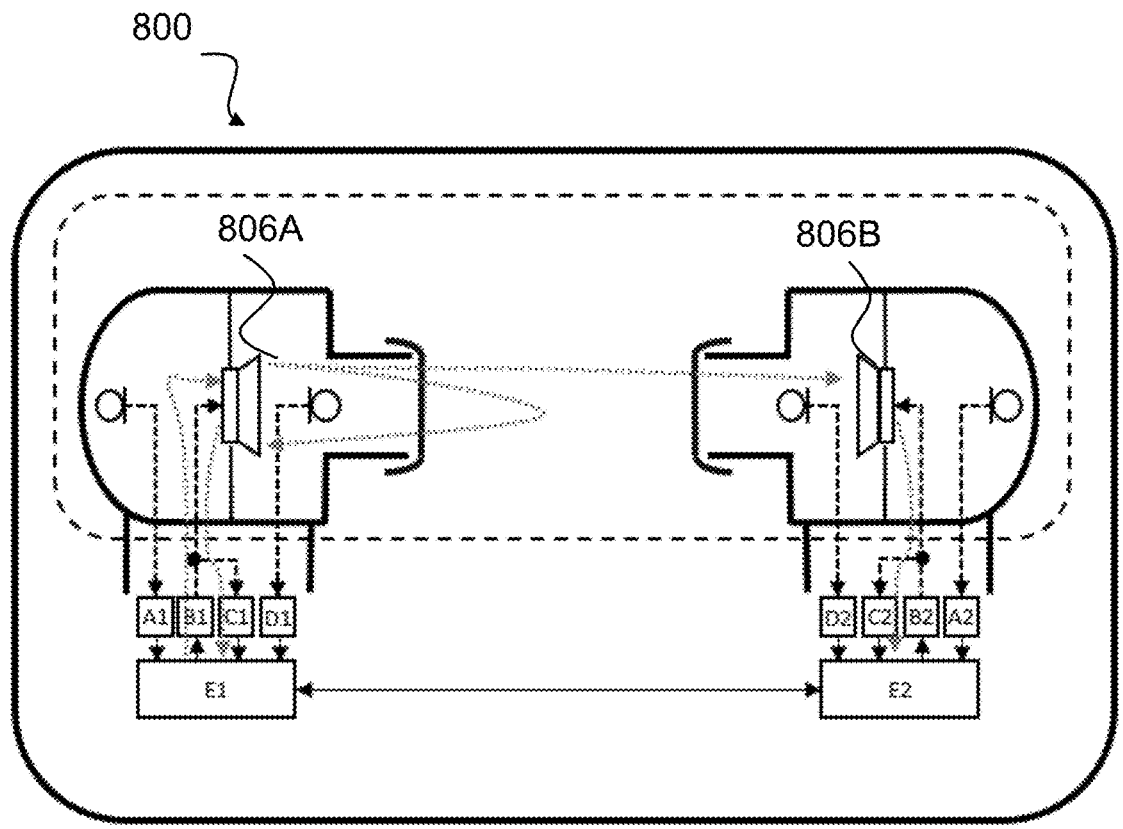
Figure 8C:
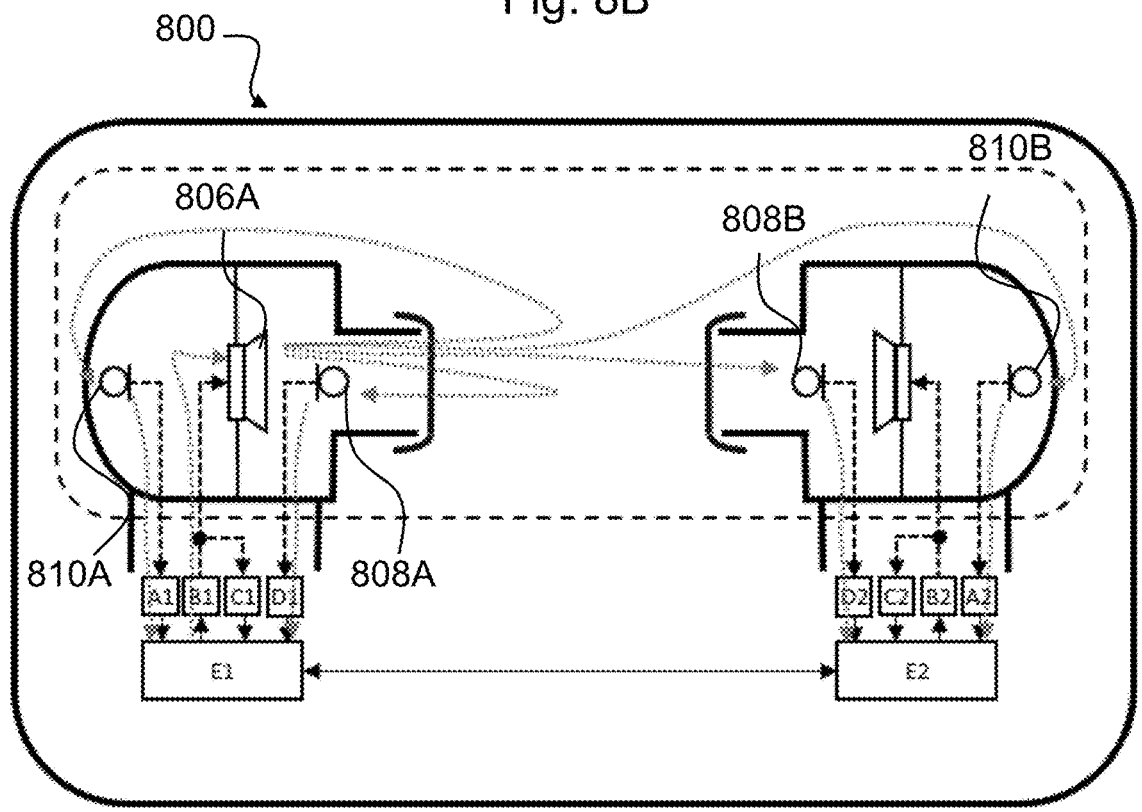

FIGS. 8A, 8B and 8C are schematic diagrams of a system 800 comprising first and second personal devices 802A, 802B disposed within an known acoustic enclosure 804, such as a charging case.

The first and second personal devices 802A, 802B each comprise respective speaker 806A, 806B, internal microphone 808A, 808B, and external microphone 810A, 810B. Each of the first and second personal devices 802A, 802B further comprises circuitry E1, E2 for generating sounds from respective speakers 806A, 806B and measuring responses from speakers and microphones 806A, 806B, 808A, 808B, 810A, 810B. Each of the first and second personal devices 802A, 802B further comprises a preamplifier and ADC A1, A2 for converting a signal derived from the external microphone 810A, 810B into a digital signal, a DAC and amplifier B1, B2 for applying a voltage on the terminals of the respective speakers 806A, 806B, a circuit for using the speaker 806A, 806B as a transducer, C1, C2 and preamplifier and ADC D1, D2 for converting a signal derived from the internal microphone 808A, 808B into a digital signal.

For example, as illustrated in FIG. 8B, in some embodiments, an acoustic stimulus is generated by speaker 806A via DAC and amplifier B1, a first response signal is derived from the speaker 806A via the circuit C1, and a second response signal is derived from the speaker 806B via the circuit C2.

As illustrated in FIG. 8C, in some embodiments, an acoustic stimulus is generated by speaker 806A via DAC and amplifier Bl, a first response signal is derived from the internal microphone 808A via preamplifier and ADC D1, a second response signal is derived from the external microphone 810A via preamplifier and ADC A1, and a third response signal is derived from internal microphone 808B preamplifier and ADC D2, and a fourth response signal is derived from internal microphone 810B via preamplifier and ADC A2.

Figure 9:
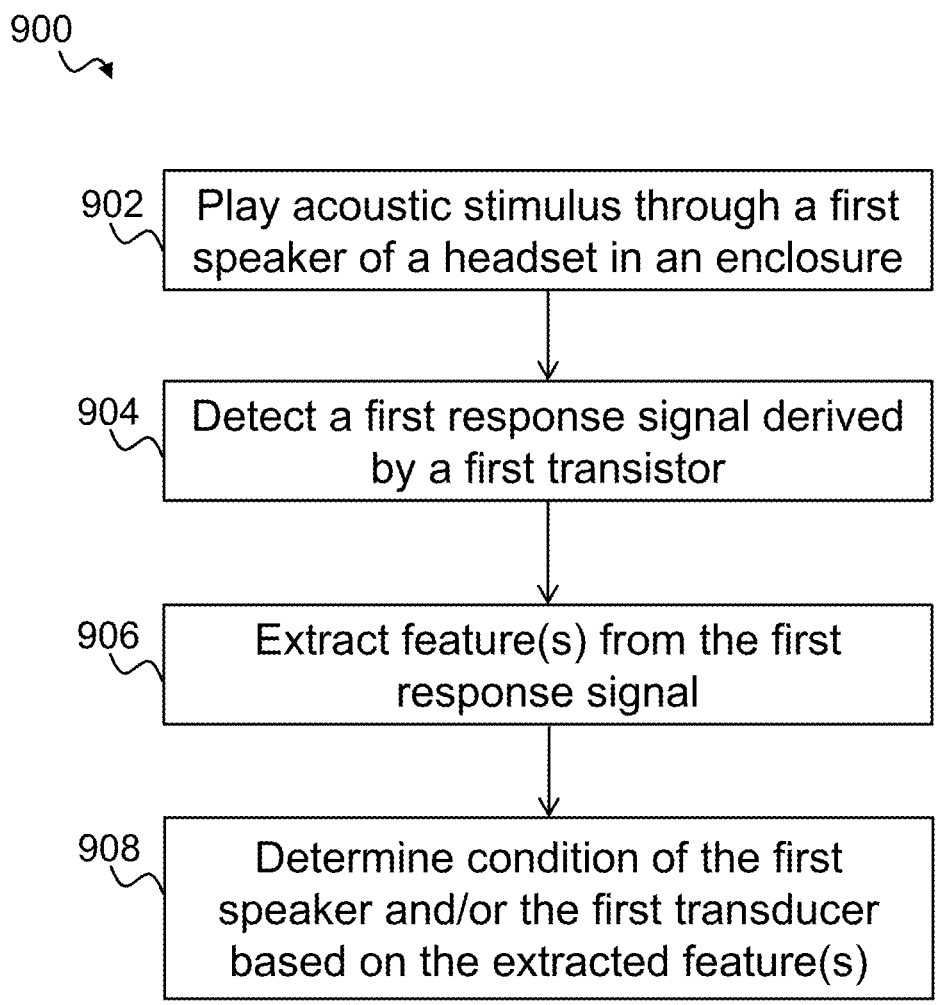
FIG. 9 is a flow diagram of a process according to embodiments of the present disclosure.

FIG. 9 is a flow diagram of a process 900 which may be performed by the system 700 shown in FIG. 7 and the system of 800 FIGS. 8A, 8B and 8C.

At step 902, the system 700, 800 generates and applies an acoustic stimulus using the transducer 60 when the system 800 is enclosed in the acoustic enclosure 804. For example, the acoustic stimulus is played through the first speaker 806A of the first personal audio device 802A of the system 800.

At step 904, the system 700, 800 receives a response signal to the acoustic stimulus which is incident at a transducer of the system 700, 800. The response signal comprises a component of the acoustic stimulus reflected from features in the acoustic path of the respective transducer.

In some embodiments, the system 700 detects a first response signal derived by the first speaker 806A or by a first microphone 808A, 808B such as an external microphone, or a second microphone 810A, 810B of the system 800. In some embodiments, the system 800 detects a first response signal derived by the first speaker 806A of the system 800 and a second response signal derived by the first microphone 808A, 810B or the second microphone 810A, 810B. In some embodiments, the system 800 detects a first response signal derived by the first microphone 808A, 808B and a second response signal derived by a second microphone 810A, 810B. In some embodiments, the system 700 detects a first response signal derived by the first speaker 806A and a second response signal derived by the first microphone 808A, 808B and a third response signal derived by the second microphone 810A, 810B. In some embodiments, the system 700 may further determine a fourth response signal derived from a further microphone 808A, 808B,810A, 8101B.

In some embodiments, the first, second and/or third microphones are microphones of the first personal audio device 802A of the system 800 or are microphones of a second personal audio device 802B of the system 800, which substantially conforms to first personal audio device 802A (and system 700), and is also enclosed in the acoustic enclosure. In some embodiments, a first or further response signal is derived by speaker 806B of the second personal audio device 802B.

In some embodiments, the second personal audio device 802B generates and applies a second acoustic stimulus using a speaker 806B of the second personal audio device 802B, which is detected by one or more transducers 806A, 806B, 808A, 808B, 810A, 810B of the first and/or second personal audio devices 802A, 802B. For example, a response signal to the second acoustic stimulus may be derived by one or more of the speaker 806A, 806B of the first and/or second personal audio devices 802A, 802B, and/or microphone(s) 808A, 808B, 810A, 810B of the first and/or second personal audio devices 802A, 802B.

At step 906, the system 800 extracts, from the response signal(s), for example as received at the microphone 808A, 808B, 810A, 810B, one or more features for use in a diagnostic process. For example, the one or more features may comprise one or more of: a resonant frequency; a frequency response; one or more mel frequency cepstral coefficients, a feature reflectance, and a feature impendence.

At step 908, the system 800 determines a condition of the acoustic path of the transducer 806A, 806B, the microphone 808A, 808B, 810A, 810B or both. The condition may comprise a condition of one or more physical components in the acoustic path, such as a speaker grille, and/or the speaker 806A, 806B and/or the microphone 808A, 808B, 810A, 810B. The condition may be a build-up of dirt or wax in the acoustic path or an amount thereof, or that the component is impaired, faulty or has deteriorated. The condition may be determined by comparing one or more features of the response signal to corresponding one or more features of a template response signal, as may be stored in template 718. If the characteristics of the signal as indicated by the one or more features differ from the expected characteristics, for example, by greater than a threshold amount, it may be possible to deduce that the transducer 806A, 806B, 808A, 808B, 810A, 810B is impaired. In some cases, by detecting further response signals from other transducers of the system 700, 800 or another similar system 700, 800 enclosed in the same acoustic enclosure, the condition of the transducer(s) may be determined with greater certainty. Furthermore, the condition of any obstacles in the acoustic path of the transducer 806A, 806B can be estimated based on characteristics of the signal received at the microphone 808A, 808B, 810A, 810B.

In some embodiments, where the first response signal is derived from the first speaker 808A, 808B, 810A, 810B of the system 800, and the system 800 determines that the one or more features of the first response signal substantially correspond with corresponding features of a template response signal for the first speaker 808A, 808B, the system 700 determines the condition of the first speaker as being not impaired. However, in the event that the system 800 determines that the one or more features of the first response signal do not substantially correspond with corresponding features of a template response signal for the first speaker 808A, 808B, the system 800 determines the condition of the first speaker as being impaired and/or that there is some obstacle in the acoustic path of the first speaker, such as a dirty grill.

If the system 700, 800 determines that speaker 806A of the first personal audio device 802A is not impaired but that the speaker 806B of the second personal audio device 802B is impaired, the system 700, 800 may use the speaker 806A of the first personal audio device 802A to compensate for the speaker of the second personal audio device 802B. For example, the system 700, 800 will have access to a template response signal for speaker 806A when speaker 806B is being played. If it is determined that 806B is impaired, the system may rely on the template response signal for speaker 806A to make necessary compensations for that impairment. For example, an acoustic sound may be generated by speaker 806B and the associated response signal derived by speaker 806A. The derived response signal may be compared with the template response signal for speaker 806A when sound is being played from speaker 806B, and an output equalisation filter of speaker 806B may be adjusted until the derived response signal for speaker 806A corresponds substantially with the template response signal.

If the system 700, 800 determines that speaker 806A of the first personal audio device 802A is impaired, a second acoustic stimulus may be played through a second speaker 806B of the second personal audio device 802A and a response signal to the second acoustic stimulus may be derived from the second speaker 806B. If the system 700, 800 determines that the one or more features of the response signal to the second acoustic stimulus substantially correspond with corresponding features of a template response signal, the system 700 may use the speaker 806B of the second personal audio device 802A to compensate for the speaker 806A of the first personal audio device 802A.

If the system 700 determines that speaker 806A of the first personal audio device 802A is not impaired, and a second response signal to the first acoustic stimulus is derived from a first microphone 808A, 808B, 810A, 810B of the first or second personal audio device 802A, 802B, a condition of the first microphone 808A, 808B, 810A, 810B may be determined from the second response signal. For example, if the one or more features extracted from the second response signal correspond with those of the template, the system 700, 800 may determine that the first microphone 808A, 808B, 810A, 810B is not impaired. If, however, the one or more features extracted from the second response signal do not substantially correspond with those of the template, the system 700, 800 may determine that the first microphone 808A, 808B, 810A, 810B is impaired and/or that there is some obstacle in the acoustic path of the first microphone. Again, if the system 700, 800 determines that the speaker 806A of the first personal audio device 802A is not impaired but that the first microphone 808A, 808B, 810A, 810B is impaired, the system 700, 800 may use the speaker 806A of the first personal audio device 802A to compensate for the microphone 808A, 808B, 810A, 810B.

In some embodiments, where the first response signal is derived from the first microphone 808A, 808B, 810A, 810B of the system 700, 800 and the system 700, 800 determines that the one or more features of the first response signal substantially correspond with corresponding features of a template response signal for the first microphone 808A, 808B, 810A, 810B, the system 700, 800 determines the condition of the first speaker 806A and the first microphone 808A, 808B, 810A, 810B as being not impaired. However, in the event that the system 700, 800 determines that the one or more features of the first response signal do not substantially correspond with corresponding features of a template response signal for the first microphone 808A, 808B, 810A, 810B, the system 700, 800 determines that both the first speaker 806A and the first microphone 808A, 808B, 810A, 810B are potentially impaired and that there is potentially some obstacle in the acoustic path of the first microphone.

The system 700, 800 may therefore detect a second response signal to the first acoustic stimulus derived by a second microphone 808A, 808B, 810A, 810B, and determine the condition of the first speaker 806A, and the first and second microphones 808A, 808B, 810A, 810B based on the second response signal. For example, if the system 700, 800 determines that the one or more features of the second response signal substantially correspond with corresponding features of a template response signal for the second microphone 808A, 808B, 810A, 810B, the system 700, 800 may determine that the first speaker 806A and the second microphone 808A, 808B, 810A, 810B are not impaired and that the first microphone 808A, 808B, 810A, 810B is impaired and/or that there is some obstacle in the acoustic path of the first microphone 808A, 808B, 810A, 810B. Again, the system 700, 800 may use the unimpaired components of the second personal audio device 802B to compensate for impaired components of the first personal audio device 802A.

If the system 700, 800 determines that the one or more features of the second response signal do not substantially correspond with corresponding features of a template response signal for the second microphone 808A, 808B, 810A, 810B, the system 700, 800 may determine that the first speaker 806A, and the first and second microphone 808A, 808B, 810A, 810B are all impaired and/or that there is some obstacle in the acoustic path of the speaker 806A. Alternatively, the system 700, 800 may detect a further response signal to the first acoustic stimulus derived by a further speaker 806B and/or microphone 808A, 808B, 810A, 810B.

In some embodiments, a second acoustic stimulus is played to a second speaker 806A, 806B of the first or second personal audio device 802A, 802B and the system 700, 800 detects a response signal to the second acoustic stimulus derived by the second speaker 806A, 806B and determines a condition of the second speaker 806A, 806B. Assuming the condition of the second speaker 806A, 806B is not impaired, the system 700, 800 may use the second speaker 806A, 806B to compensate for the impaired components of the first or second personal audio devices 802A, 802B.

In some embodiments, where components (speaker(s) and/or microphone(s)) of the second personal audio device 802B are being used to determine the condition of the components of the first personal audio device 802A, the first personal audio device 802Amay be configured to receive diagnostic data, which may include for example, a response signal (or one or more features extracted from a response signal) derived from a transducer of the second personal audio device 802B, from the diagnostics module 716 of the second personal audio device 802B via transceiver 726.

In some embodiments, the system 700, 800 may perform, adjust, update or otherwise augment an acoustic enhancement process being performed by the control module 702 based on the condition of the components and/or acoustic path determined at step 908.

Embodiments may be implemented in an electronic, portable and/or battery powered host device such as a smartphone, an audio player, a mobile or cellular phone, a handset. Embodiments may be implemented on one or more integrated circuits provided within such a host device. Embodiments may be implemented in a personal audio device configurable to provide audio playback to a single person, such as a smartphone, a mobile or cellular phone, headphones, earphones, etc. See FIGS. 1a to 1e. Again, embodiments may be implemented on one or more integrated circuits provided within such a personal audio device. In yet further alternatives, embodiments may be implemented in a combination of a host device and a personal audio device. For example, embodiments may be implemented in one or more integrated circuits provided within the personal audio device, and one or more integrated circuits provided within the host device.

It should be understood—especially by those having ordinary skill in the art with the benefit of this disclosure—that the various operations described herein, particularly in connection with the figures, may be implemented by other circuitry or other hardware components. The order in which each operation of a given method is performed may be changed, and various elements of the systems illustrated herein may be added, reordered, combined, omitted, modified, etc. It is intended that this disclosure embrace all such modifications and changes and, accordingly, the above description should be regarded in an illustrative rather than a restrictive sense.

Similarly, although this disclosure makes reference to specific embodiments, certain modifications and changes can be made to those embodiments without departing from the scope and coverage of this disclosure. Moreover, any benefits, advantages, or solutions to problems that are described herein with regard to specific embodiments are not intended to be construed as a critical, required, or essential feature or element.

Further embodiments and implementations likewise, with the benefit of this disclosure, will be apparent to those having ordinary skill in the art, and such embodiments should be deemed as being encompassed herein. Further, those having ordinary skill in the art will recognize that various equivalent techniques may be applied in lieu of, or in conjunction with, the discussed embodiments, and all such equivalents should be deemed as being encompassed by the present disclosure.

The skilled person will recognise that some aspects of the above-described apparatus and methods, for example the discovery and configuration methods may be embodied as processor control code, for example on a non-volatile carrier medium such as a disk, CD- or DVD-ROM, programmed memory such as read only memory (Firmware), or on a data carrier such as an optical or electrical signal carrier. For many applications embodiments of the invention will be implemented on a DSP (Digital Signal Processor), ASIC (Application Specific Integrated Circuit) or FPGA (Field Programmable Gate Array). Thus the code may comprise conventional program code or microcode or, for example code for setting up or controlling an ASIC or FPGA. The code may also comprise code for dynamically configuring re-configurable apparatus such as re-programmable logic gate arrays. Similarly the code may comprise code for a hardware description language such as Verilog TM or VHDL (Very high speed integrated circuit Hardware Description Language). As the skilled person will appreciate, the code may be distributed between a plurality of coupled components in communication with one another. Where appropriate, the embodiments may also be implemented using code running on a field-(re)programmable analogue array or similar device in order to configure analogue hardware.

Note that as used herein the term module shall be used to refer to a functional unit or block which may be implemented at least partly by dedicated hardware components such as custom defined circuitry and/or at least partly be implemented by one or more software processors or appropriate code running on a suitable general purpose processor or the like. A module may itself comprise other modules or functional units. A module may be provided by multiple components or sub-modules which need not be co-located and could be provided on different integrated circuits and/or running on different processors.

It should be noted that the above-mentioned embodiments illustrate rather than limit the invention, and that those skilled in the art will be able to design many alternative embodiments without departing from the scope of the appended claims or embodiments. The word "comprising" does not exclude the presence of elements or steps other than those listed in a claim or embodiment, "a" or "an" does not exclude a plurality, and a single feature or other unit may fulfil the functions of several units recited in the claims or embodiments. Any reference numerals or labels in the claims or embodiments shall not be construed so as to limit their scope.

As used herein, when two or more elements are referred to as "coupled" to one another, such term indicates that such two or more elements are in electronic communication or mechanical communication, as applicable, whether connected indirectly or directly, with or without intervening elements.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative. Accordingly, modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described above.

Unless otherwise specifically noted, articles depicted in the drawings are not necessarily drawn to scale.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

Although specific advantages have been enumerated above, various embodiments may include some, none, or all of the enumerated advantages. Additionally, other technical advantages may become readily apparent to one of ordinary skill in the art after review of the foregoing figures and description.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

The invention claimed is:

1. A method for diagnosing a condition of a first headset, the method comprising:
   playing a first audio stimulus through a first speaker of the first headset while the first headset is enclosed in a headset enclosure;
   detecting a first response signal derived by a first transducer while the first headset is enclosed in the headset enclosure; and
   determining, by the first headset and/or the headset enclosure, a condition of the first speaker and/or first transducer based on the first response signal, wherein the condition is whether or not the respective first speaker and/or first transducer is impaired.

2. The method of claim 1, wherein determining the condition comprises comparing the first response signal to a template first response signal.

3. The method of claim 2, wherein determining the condition further comprises extracting one or more features of the first response signal, and
   wherein comparing the first response signal to the template first response signal comprises comparing the one or more features extracted features with a corresponding template feature, the corresponding template features representing an optimal condition of the acoustic path or a previous condition of the acoustic path.

4. The method of claim 1, wherein the first transducer is the first speaker and the method further comprises:
   responsive to determining that the first response signal corresponds substantially to a template response signal, determining the condition of the first speaker as being not impaired; and
   responsive to determining that the first response signal does not correspond substantially to a template first response signal, determining the condition of the first speaker as being impaired.

5. The method of claim 1, wherein the first transducer is the first speaker and the method further comprises:
   determining that the first response signal corresponds substantially to a template response signal;
   determining the condition of the first speaker as being not impaired;
   detecting a second response signal to the first audio stimulus derived by a second speaker;
   determining that the second response signal does not correspond substantially to the template second response signal; and
   determining a condition of the second speaker as being impaired.

6. The method of claim 5, further comprising using the first speaker to compensate for the second speaker.

7. The method of claim 1, wherein the first transducer is the first speaker and the method further comprises:
   determining that the first response signal corresponds substantially to a template response signal;
   determining the condition of the first speaker as being impaired;
   playing a second audio stimulus through a second speaker of the headset;
   detecting a third response signal to the second audio stimulus derived by the second speaker;
   determining that the third response signal corresponds substantially to the template third response signal; and
   using the second speaker to compensate for the first speaker.

8. The method of claim 1, wherein the first transducer is the first speaker and the method further comprises:
   determining that the first response signal corresponds substantially to a template response signal;
   determining the condition of the first speaker as being not impaired;
   detecting a fourth response signal to the first audio stimulus derived by a first microphone; and
   determining a condition of the first microphone based on the fourth response signal;
   wherein determining the condition of the first microphone based on the fourth response signal comprises:
      responsive to determining that the fourth response signal corresponds substantially to a template fourth response signal, determining the condition of the first microphone as being not impaired; and responsive to determining that the fourth response signal does not correspond substantially to the template fourth response signal, determining the condition of the first microphone as being impaired.

9. The method of claim 8, further comprising using the first speaker to compensate for the first microphone.

10. The method of claim 1, wherein the first transducer is a first microphone and the method further comprises:
responsive to determining that the first response signal corresponds substantially to a template first response signal, determining the condition of the first microphone as being not impaired and a condition of the first speaker as being not impaired; and
responsive to determining that the first response signal does not correspond substantially to a template first response signal, determining the condition of the first microphone as being potentially impaired and the condition of the first speaker as being potentially impaired.

11. The method of claim 1, wherein the first transducer is a first microphone and the method further comprises:
determining that the first response signal does not correspond substantially to a template first response signal;
determining the condition of the first microphone as being potentially impaired and the condition of the first speaker as being potentially impaired;
detecting a second response signal derived by a second microphone; and
determining the condition of the first speaker and/or the first microphone and/or the second microphone based on the second response signal.

12. The method of claim 11, further comprising:
determining that the second response signal corresponds substantially to a template second response signal; and
determining the condition of the first microphone as being impaired, the condition of the first speaker as being not impaired and a condition of the second microphone as being not impaired.

13. The method of claim 12, further comprising using the first speaker and/or the second microphone to compensate for the first microphone.

14. The method of claim 11, further comprising:
determining that the second response signal does not correspond substantially to a template second response signal; and
determining the condition of the second microphone as being potentially impaired.

15. The method of claim 11, further comprising:
determining that the second response signal does not correspond substantially to a template second response signal; and
determining the condition of the first speaker as being impaired, the condition of the first microphone as being unimpaired and a condition of the second microphone as being unimpaired.

16. The method of claim 1, wherein the first transducer is a first microphone and the method further comprises:
determining that the first response signal does not correspond substantially to a template first response signal;
determining the condition of the first microphone as being potentially impaired and the condition of the first speaker as being potentially impaired;
playing a second audio stimulus through a second speaker of the headset;
detecting a fifth response signal to the second audio stimulus derived by the second speaker; and
determining that the fifth response signal corresponds substantially to the template fifth response signal; and
using the second speaker to compensate for the first speaker and/or the first microphone.

17. The method of claim 1, wherein the first transducer is a second speaker and the method further comprises:
responsive to determining that the first response signal corresponds substantially to a template first response signal, determining the condition of the first speaker as being not impaired and a condition of the second speaker as being not impaired; and
responsive to determining that the first response signal does not correspond substantially to a template first response signal, determining the condition of the first speaker as being potentially impaired and a condition of the second speaker as being potentially impaired.

18. The method of claim 1, wherein the first transducer is a second speaker and the method further comprises:
determining that the first response signal does not correspond substantially to a template first response signal;
determining the condition of the first speaker as being potentially impaired and a condition of the second speaker as being potentially impaired;
detecting a second response signal derived by a first microphone; and
determining the condition of the first speaker and/or the first microphone and/or the second speaker based on the second response signal.

19. The method of claim 1, further comprising, prior to playing the first audio stimulus through the first speaker of the first headset while the first headset is enclosed in the headset enclosure:
detecting that the first headset is within the headset enclosure.

20. The method of claim 1, wherein the headset enclosure is a charging case.

21. An apparatus, comprising processing circuitry and a non-transitory machine-readable which, when executed by the processing circuitry, cause the apparatus to:
play a first audio stimulus through a first speaker of a first headset enclosed in a headset enclosure;
detect a first response signal derived by a first transducer enclosed in the headset enclosure; and
determine, by the first headset and/or the headset enclosure, a condition of the first speaker and/or the first transducer based on the first response signal, wherein the condition is whether or not the respective first speaker and/or first transducer is impaired.

22. A non-transitory machine-readable medium storing instructions which, when executed by one or more processors, cause an electronic apparatus to:
play a first audio stimulus through a first speaker of a first headset enclosed in a headset enclosure;
detect a first response signal derived by a first transducer enclosed in the headset enclosure; and
determine, by the first headset and/or the headset enclosure, a condition of the first speaker and/or the first transducer based on the first response signal, wherein the condition is whether or not the respective first speaker and/or first transducer is impaired.

* * * * *

UNITED STATES PATENT AND TRADEMARK OFFICE
CERTIFICATE OF CORRECTION

| | | |
|---|---|---|
| PATENT NO. | : 12,223,980 B2 | Page 1 of 2 |
| APPLICATION NO. | : 17/065219 | |
| DATED | : February 11, 2025 | |
| INVENTOR(S) | : Harvey et al. | |

It is certified that error appears in the above-identified patent and that said Letters Patent is hereby corrected as shown below:

In the Specification

1. In Column 18, Line 36, delete "8101B" and insert -- 810B --, therefor.

In the Claims

2. In Column 24, Line 16, in Claim 4, delete "a template response signal," and insert -- a template first response signal, --, therefor.

3. In Column 24, Lines 20-21, in Claim 4, delete "a template first response signal," and insert -- the template first response signal, --, therefor.

4. In Column 24, Line 26, in Claim 5, delete "a template response signal;" and insert -- a template first response signal; --, therefor.

5. In Column 24, Lines 32-33, in Claim 5, delete "the template second response signal;" and insert -- a template second response signal; --, therefor.

6. In Column 24, Line 41, in Claim 7, delete "a template response signal;" and insert -- a template first response signal; --, therefor.

7. In Column 24, Line 49, in Claim 7, delete "the template third response signal;" and insert -- a template third response signal; --, therefor.

8. In Column 24, Line 55, in Claim 8, delete "a template response signal;" and insert -- a template first response signal; --, therefor.

9. In Column 25, Lines 11-12, in Claim 10, delete "the condition of the first microphone" and insert Signed and Sealed this
Thirtieth Day of December, 2025

John A. Squires
*Director of the United States Patent and Trademark Office*

-- a condition of the first microphone --, therefor.

10. In Column 25, Lines 12-13, in Claim 10, delete "a condition of the first speaker" and insert -- the condition of the first speaker --, therefor.

11. In Column 25, Lines 15-16, in Claim 10, delete "a template first response signal," and insert -- the template first response signal, --, therefor.

12. In Column 25, Line 23, in Claim 11, delete "the condition of the first microphone" and insert -- a condition of the first microphone --, therefor.

13. In Column 25, Line 36, in Claim 12, delete "a condition of the second microphone" and insert -- the condition of the second microphone --, therefor.

14. In Column 25, Line 53, in Claim 15, delete "a condition of the second microphone" and insert -- the condition of the second microphone --, therefor.

15. In Column 25, Line 59, in Claim 16, delete "the condition of the first microphone" and insert -- a condition of the first microphone --, therefor.

16. In Column 26, Line 2, in Claim 16, delete "speaker; and" and insert -- speaker; --, therefor.

17. In Column 26, Lines 15-16, in Claim 17, delete "a template first response signal," and insert -- the template first response signal, --, therefor.

18. In Column 26, Lines 17-18, in Claim 17, delete "a condition of the second speaker" and insert -- the condition of the second speaker --, therefor.